(12) United States Patent
Leib et al.

(10) Patent No.: US 10,898,136 B2
(45) Date of Patent: Jan. 26, 2021

(54) MONITORING DEVICE FOR ANIMALS

(71) Applicants: Juergen Leib, Neunkirchen am Brand (DE); Michael Gruener, Neunkirchen am Brand (DE)

(72) Inventors: Juergen Leib, Neunkirchen am Brand (DE); Michael Gruener, Neunkirchen am Brand (DE)

( * ) Notice: Subject to any disclaimer, the term of this patent is extended or adjusted under 35 U.S.C. 154(b) by 323 days.

(21) Appl. No.: 15/382,370

(22) Filed: Dec. 16, 2016

(65) Prior Publication Data

US 2017/0095206 A1    Apr. 6, 2017

Related U.S. Application Data

(63) Continuation of application No. PCT/EP2015/063494, filed on Jun. 16, 2015.

(30) Foreign Application Priority Data

Jun. 16, 2014    (DE) .................. 10 2014 108 443

(51) Int. Cl.
*A61B 5/00* (2006.01)
*G16H 40/63* (2018.01)
(Continued)

(52) U.S. Cl.
CPC .......... *A61B 5/6822* (2013.01); *A01K 11/008* (2013.01); *A01K 27/009* (2013.01); *A01K 29/005* (2013.01); *A61B 5/0031* (2013.01); *A61B 5/02055* (2013.01); *A61B 5/02438* (2013.01); *A61B 5/0476* (2013.01); *A61B 5/11* (2013.01); *A61B 5/14532* (2013.01); *A61B 5/14542* (2013.01); *A61B 5/443* (2013.01); *B06B 1/02* (2013.01); *G16H 40/63* (2018.01); *H02N 2/18* (2013.01); *A61B 5/0024* (2013.01);
(Continued)

(58) Field of Classification Search
CPC combination set(s) only.
See application file for complete search history.

(56) References Cited

U.S. PATENT DOCUMENTS 5,609,156 A * 3/1997 Keith .................. A61B 5/0444
                                                    600/483
6,044,795 A * 4/2000 Matsuura ................ A01K 5/02
                                                    119/51.02

(Continued)

FOREIGN PATENT DOCUMENTS

CA        2591902 A1    12/2008
DE    102012017919 A1    3/2014

OTHER PUBLICATIONS

International Search Report dated Sep. 10, 2015 of international application PCT/EP2015/063494 on which this application is based.

*Primary Examiner* — Niketa I Patel
*Assistant Examiner* — Shirley X Jian
(74) *Attorney, Agent, or Firm* — Walter Ottesen, P.A.

(57) ABSTRACT

A monitoring device for monitoring the well-being of animals, the monitoring device including a carrier arrangement which can be attached to an animal and which has at least one sensor for sensing a vital function of an animal wearing the carrier arrangement. In the event of a deviation of an actual state from a target state of the animal that leaves a tolerance range, an output signal signaling the deviation is outputted by an output unit.

22 Claims, 6 Drawing Sheets

(51) Int. Cl.
*A61B 5/024* (2006.01)
*B06B 1/02* (2006.01)
*A01K 11/00* (2006.01)
*A01K 27/00* (2006.01)
*A01K 29/00* (2006.01)
*A61B 5/0205* (2006.01)
*A61B 5/0476* (2006.01)
*A61B 5/11* (2006.01)
*A61B 5/145* (2006.01)
*H02N 2/18* (2006.01)
*A61B 5/08* (2006.01)

(52) U.S. Cl.
CPC .......... *A61B 5/0205* (2013.01); *A61B 5/0816* (2013.01); *A61B 2503/40* (2013.01); *A61B 2560/0214* (2013.01); *A61B 2562/0219* (2013.01)

(56) References Cited

U.S. PATENT DOCUMENTS

| | | | |
|---|---|---|---|
| 6,252,336 B1 | 6/2001 | Hall | |
| 7,705,736 B1* | 4/2010 | Kedziora | A01K 11/008 340/573.3 |
| 8,663,106 B2* | 3/2014 | Stivoric | A61B 5/6833 600/301 |
| 9,275,534 B2 | 3/2016 | Alasaarela | |
| 9,526,437 B2* | 12/2016 | Tupin, Jr. | A01K 27/009 |
| 10,070,627 B2* | 9/2018 | Tupin, Jr. | A01K 27/009 |
| 10,149,617 B2* | 12/2018 | Couse | A01K 29/005 |
| 2002/0010390 A1* | 1/2002 | Guice | A01K 11/008 600/300 |
| 2003/0018241 A1* | 1/2003 | Mannheimer | A61B 5/02455 600/300 |
| 2005/0245839 A1* | 11/2005 | Stivoric | G01K 1/024 600/549 |
| 2006/0249088 A1* | 11/2006 | Eu | A01K 1/033 119/51.02 |
| 2008/0058670 A1* | 3/2008 | Mainini | A61B 5/0002 600/549 |
| 2008/0202445 A1 | 8/2008 | Rugg | |
| 2010/0036277 A1* | 2/2010 | Austin | A61D 13/00 600/549 |
| 2010/0179454 A1* | 7/2010 | Davies | A01K 11/008 600/595 |
| 2011/0139088 A1* | 6/2011 | Gordon | A01K 13/003 119/720 |
| 2012/0059235 A1* | 3/2012 | Davies | A01K 11/008 600/364 |
| 2012/0271129 A1* | 10/2012 | Wang | A61B 5/14551 600/323 |
| 2013/0014706 A1* | 1/2013 | Menkes | A61D 13/00 119/859 |
| 2013/0281796 A1 | 10/2013 | Pan | |
| 2013/0321168 A1 | 12/2013 | Mahony et al. | |
| 2014/0107434 A1* | 4/2014 | Mottram | A01K 11/00 600/301 |
| 2014/0123912 A1 | 5/2014 | Menkes et al. | |
| 2014/0182519 A1* | 7/2014 | Tupin, Jr. | A01K 27/009 119/859 |
| 2014/0267299 A1* | 9/2014 | Couse | G06T 11/206 345/440.2 |
| 2014/0275824 A1* | 9/2014 | Couse | A01K 29/005 600/301 |
| 2014/0276127 A1* | 9/2014 | Ferdosi | A61B 5/0245 600/483 |
| 2015/0181840 A1* | 7/2015 | Tupin, Jr. | A01K 27/009 600/483 |
| 2016/0198960 A1 | 7/2016 | Menkes | |
| 2017/0262599 A1* | 9/2017 | Grisel | G16H 50/20 |

* cited by examiner

MONITORING DEVICE FOR ANIMALS

CROSS REFERENCE TO RELATED APPLICATIONS

This application is a continuation application of international patent application PCT/EP2015/063494, filed Jun. 16, 2015, designating the United States and claiming priority from German application 10 2014 108 443.8, filed Jun. 16, 2014, and the entire content of both applications is incorporated herein by reference.

FIELD OF THE INVENTION

The invention generally relates to the care, monitoring and optimization of activity, health, vitality, well-being, behavior, fitness, and safety (referred to as "well-being" below) of domestic and farm animals (referred to as "animals" below). More particularly, the invention relates to an electronic device for detecting and monitoring the well-being of animals and displaying the status and autonomously deriving recommendations, for example, on care.

BACKGROUND OF THE INVENTION

Domestic animals, especially dogs and horses, possess a high value as a companion of humans. The well-being of the animal has therefore become very important for the animal owner. In the field of farm animal management, monitoring of the health status and well-being is important to the animal owner as well. However, it is often not easy for the animal owner or caretaker to see whether the animal is comfortable and completely healthy. If an animal is not completely healthy, physical overstress can have far-reaching consequences and the condition of the animal may deteriorate.

Therefore, many animal owners desire to be well-informed about the well-being of the animal.

In case of a deviation from the normal or ideal status it is important for the animal owner to know how the animal's condition changes and whether measures are necessary in order to restore the normal or ideal status, for example, action, medication, exercise therapies, nutritional and weight optimization measures, care optimization measures, and/or to monitor the influence and effect of such measures.

In addition to the health status of the animal, there is also a demand from animal owners in case of their absence to be informed about whether the animal is in a dangerous and/or unusual situation, for example when the animal is left alone or in foreign care, so that the animal owner can ensure that the well-being of not personally supervised animals is ensured and can inform himself whether the animal feels uncomfortable or is in danger.

From United States patent application publications 2013/0014706 and 2016/0198960, a system is known comprising an animal collar for monitoring health and vital signs including a warning and diagnostic function. The collar measures body functions, such as respiration, pulse, temperature, and movement and includes a processor that interprets the results. According to an embodiment of the invention, the system can moreover compare its own physiological data with comparative data of the respective animal breed.

Generally, there is the problem that in animals physiological data and vital functions, such as from optical or acoustic blood/pulse measurement, ECG, body temperature, breathing noises, and respiration rate, oxygen saturation, (skin) moisture (referred to as "vital function" in this text) can vary very significantly. For example the pulse rate may vary strongly depending on the animal species and breed, but also depending on the age of the animal and other factors. Furthermore, data may not be available for every animal breed, or the animal may not be classifiable into a particular breed for which data are available. For instance dogs exhibit an enormous variability in body habitus because of the large number of dog breeds. Alone the size and the weight vary by more than one order of magnitude between dog breeds. The different physique causes correspondingly different vital functions, such as strongly varying pulse and respiration rates. For example, for dogs the resting pulse is between 70 and 160 beats per minute, depending on the breed.

SUMMARY OF THE INVENTION

It is an object of the invention to enable safe and reliable monitoring of the well-being of animals with as little a-priori knowledge as possible.

With the invention, a target state of the animal is determined which is independent of the variability of the vital functions that is particularly large in the case of domestic animals. In its basic functions the invention is therefore independent of comparative data of other animals. The monitoring device autonomously learns which values the vital functions should have according to the target state of the animal. The device according to the invention is therefore very independent of the animal breed or even the animal species for which the collar is used.

Accordingly, the invention, for example, provides a monitoring device for monitoring vital functions, in particular the well-being of animals and/or behavior patterns of animals, comprising:

at least one carrier arrangement attachable to an animal and comprising at least one sensor for sensing a vital function of an animal that wears the carrier arrangement, and an evaluation unit in communication with the at least one sensor; and an output unit for outputting an output signal;

wherein the evaluation unit furthermore comprises a signal generator and a memory; wherein the signal generator is adapted to output signals at time intervals; and the evaluation unit is adapted to respond to a signal from the signal generator to record at least one measured value of a vital function captured by the sensor and to store in the memory and add to previously recorded data a data item representing the measured value or corresponding to the measured value; wherein the evaluation unit is furthermore adapted to access the data stored in the memory and to define at least one target state on the basis of the data, in particular a target state of the vital function of the animal; and to determine an actual state on the basis of the data acquired after the definition of the target state and stored in the memory; and to compare the actual state with the target state; and in the event that a deviation of the actual state from the target state of the animal leaves a tolerance range, or in the event of a correspondence between an actual state (17) and a target state, to output an output signal via the output unit, which signals the deviation or correspondence.

According to a preferred embodiment, a sensor of the monitoring device is configured as an autonomous sensor node in a network of sensors, which is preferably controlled by the evaluation unit. In addition to the actual active or passive signal pickup, such a sensor in the form of a sensor node comprises a power supply, analog and/or digital signal processing, an analog and/or digital signal memory, and a timer clocking and/or synchronizing the autonomous measurement. The sensor node furthermore includes an interface for connection, in wired, wireless, and/or optical fashion to the network of sensors and evaluation unit. This interface may have an analog and/or volatile and/or non-volatile digital buffer memory. A sensor status display provides information about signal quality of the measurements, the state of local power supply and information about the connectivity of the interface directly on the sensor, and/or provides the sensor status via the interface.

Therefore, according to one aspect of the invention there is also provided a monitoring device for monitoring vital functions, comprising at least one sensor in the form of an autonomous sensor node which can be attached on an animal for detecting a vital function, the sensor node comprising at least one signal pickup for acquiring the measured values characterizing the vital function;
at least one autonomous and/or central power supply;
at least one analogue and/or digital interface; and
at least one analogue and/or digital timer; wherein the sensor node is further adapted to be connected, at least temporarily, to a wired and/or wireless and/or optical network with an evaluation unit preferably attachable to the animal separately from the sensor node and/or with at least one further autonomous sensor node that is attachable to the animal separately from the sensor node.

Optionally, the device can furthermore be used to perform an evaluation and/or validation and/or support for the interpretation of the status using additional information.

According to an embodiment, the output signal may be triggered autonomously, that is in response to a deviation leaving the tolerance range, and/or time-controlled, or else by the user. According to a further embodiment, the output may be addressed to the monitored animal or to other monitored animals in order to give feedback to the respective animal. It may also be addressed to the user or other users as an information.

The monitored vital functions, such as optical or acoustic blood/pulse measurement, ECG, body temperature, breathing noises, and respiration rate, oxygen saturation, (skin) moisture, may furthermore be put in relation to at least one data item or further data (referred to as "additional information" below), so as to obtain information about the condition and well-being of the monitored animal, for displaying them and, if necessary, initiating autonomous actions or action recommendations. Such additional information may include, for example, position and movement data, ambient data (such as temperature or weather, motion detector signals, ambient noise/acoustic signals), data of further monitored animals or data from other devices, for example, food dispensers. With regard to such additional information, the evaluation unit according to an embodiment of the invention may therefore be configured to acquire further data from at least one external data source, in addition to the data captured by the at least one sensor, and to take them into account when comparing the target state with the actual state or when checking whether a deviation of these states exceeds the tolerance range. One example is the determination of the ambient temperature or else of the time of day or the season. All of these parameters generally have an influence on vital functions, so that the tolerance range or even the actual state, for example, may be adapted depending on these external data. Optionally, the comparison may even be discarded or omitted, for example if the external data show that a momentary deviation of the actual state from the target state does not have a health-damaging and/or health-impairing cause. To mention an example, this might be a sound event detected by an external microphone, which scares the animal so that the pulse rate increases. Another example is the ambient temperature detected by an external sensor or by a sensor that is a component of the monitoring and diagnostic device. If the ambient temperature is very high, this will also have an impact on the pulse rate. This can then be taken into account in the determination of the actual state. In particular external data such as the ambient temperature may form part of the actual state.

According to an embodiment of the invention, the signal generator may be configured as a timer. In this way, the measured values can be recorded in periodic time intervals or at specific times of the day.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
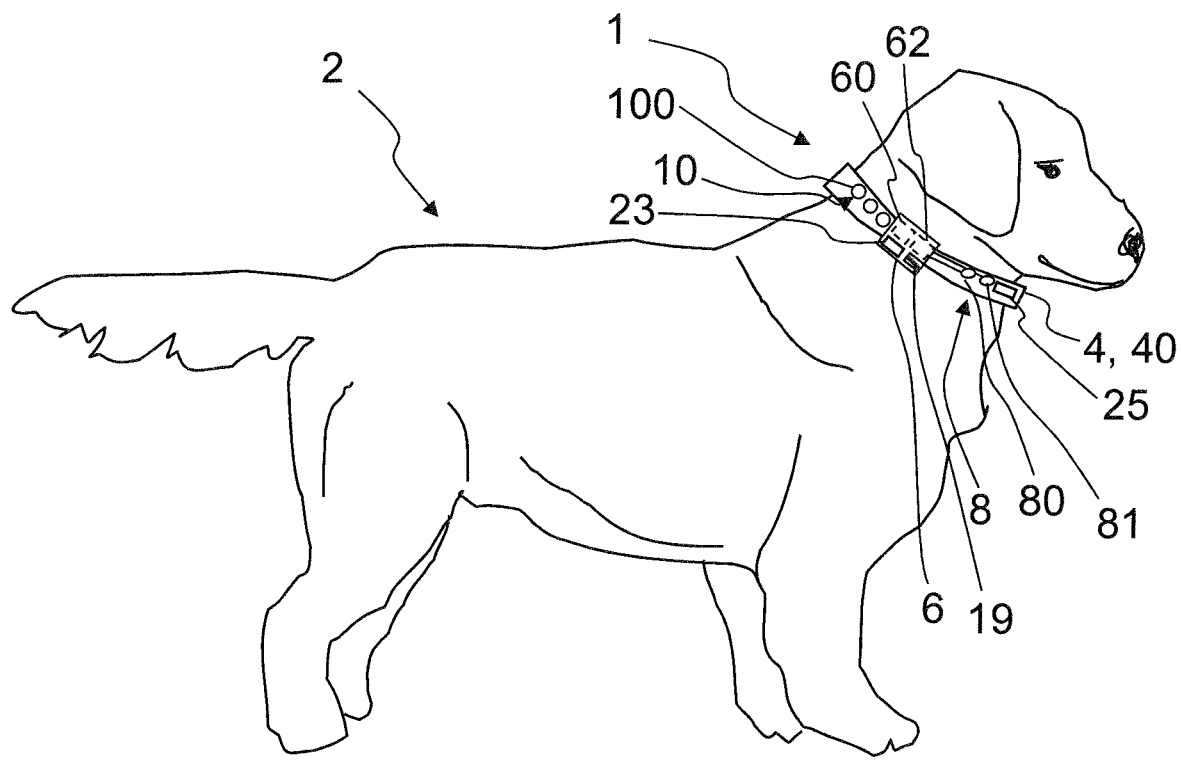
FIG. 1 shows a domestic animal with a first embodiment of the invention.

According to a particularly preferred embodiment, the carrier arrangement for the sensor is configured as an animal collar and/or harness and/or halter. Such a collar can be flexibly adapted to different animals of even substantially different sizes. A particularly preferred application of the invention is the monitoring of the well-being of dogs. FIG. 1 shows an embodiment for this case. According to the aforementioned embodiment, the carrier arrangement 4 is therefore configured as a dog collar 40. Carrier arrangement 4 comprises a sensor 8 which measures at least one vital function of the animal 2. Preferably, at least the pulse rate of the animal 2 is sensed via a pulse rate sensor 80.

According to yet another embodiment of the invention, the evaluation unit 6 is also attached to the animal 2 using the carrier arrangement 4 and is in particular integrated within the carrier arrangement 4. This embodiment is also implemented in the example shown in FIG. 1.

Alternatively or additionally, the output unit 10 may also be attached to the animal 2 using the carrier arrangement 4, without being limited to the specific example shown in FIG. 1. The signal of the output unit 10 may be a visual and/or acoustic and/or electrical and/or pneumatic and/or vibration signal. For example light-emitting diodes 100 may be used as the output unit 10, as is the case in the example shown in FIG. 1.

As in the example shown, carrier arrangement 4, sensor 8, evaluation unit 6 and output unit 10 may thus form a unit. In other words, sensor 8, evaluation unit 6, and output unit 10 are integrated in the carrier arrangement 4. The evaluation unit can include a data storage unit which can serve as a memory. Signal generator 60, for example a clock generator of the evaluation unit 6 now outputs signals at time intervals. In response to these signals, measured values of sensor 8 are recorded and stored in the memory 62 of evaluation unit 6 as data representing the measured values or corresponding to the measured values. According to an embodiment of the invention, these measured values include the pulse rates of the animal 2. For example, the recording may take place every minute or every hour.

The evaluation unit 6 then determines a target state from a plurality of data of the vital functions. It is possible to determine a target state which represents the condition of the animal already from the data of only one vital function, such as the pulse rate. In particular, this may be accomplished easily by a statistical evaluation of the data. Without being limited to the embodiments, it is therefore contemplated according to a further embodiment of the invention that the evaluation unit 6 is adapted for statistically evaluating data stored in memory 62 and to determine a target state by taking into account at least one statistical parameter obtained in the evaluation. Such statistical parameters may in particular include an average, a variance, a full width at half maximum of a frequency distribution, or a correlation coefficient.

The evaluation unit 6 may enhance the quality of the measurement by combining measured values from different sensors 8 and additional information. For example, the sampling rate and intensity of, for example, the optical pulse measurement will be increased when the motion sensor indicates strong activity.

The evaluation unit 6 may furthermore be configured to selectively switch off sensors in order to save energy. For example, the optical pulse measurement for determining the resting pulse can be omitted when the motion sensor senses low activity and the acoustic pulse measurement provides good signal quality. Also, the evaluation unit 6 may trigger measurements of further sensors 8 or of external sensors which permit a further interpretation of the measurements.

After determination of the target state by evaluation unit 6, further measured values of the sensor 8 are recorded in response to signals from signal generator 60 and stored in memory 62. Based on these later recorded values, the evaluation unit 6 now determines an actual state of the vital function in the same manner as for the target state and compares it with the target state. If the evaluation unit 6 now detects a deviation of the actual state from the target state, which exceeds a predetermined tolerance range, this is intended to be signaled to the animal owner via output unit 10, so that the latter can provide medical care for the animal as early as possible or take measures to keep the animal healthy or to return it to a healthy state as quickly as possible. The signal may be triggered solely on the basis of the measured vital data or on the basis of a verification/interpretation of the vital data using ambient data or external data.

As shown in FIG. 1, this output unit 10 may simply comprise one or more light-emitting elements, preferably light-emitting diodes 100. Various forms of signaling are conceivable here. In the simplest form, a critical state of the animal could be indicated simply by illumination of the light-emitting elements. Furthermore, color changes, brightness changes, or flashing patterns are possible. The latter measures moreover permit to signal to the animal owner the amount of deviation from the tolerance range in a very simple manner. For example, slow flashing of the light-emitting diodes 100 could indicate a slight deviation. In this case, the animal owner may simply wait and see whether the condition of the animal returns to its normal state. Fast flashing, by contrast, may indicate that the animal is miserable and the animal owner should immediately check the state of health/well-being of the animal.

In order to improve the options of data evaluation, an interface 19 may furthermore be provided, without being limited to the particular embodiment illustrated. Via this interface, for example, a USB interface, the data stored in memory 62 can be read out. It is also contemplated that data can be written into the memory via interface 19. For example it would be possible in this way to generate or overwrite a target state. In the event of a replacement of the carrier arrangement 4, for example, the data set of the animal 2 existing so far can be restored in this way.

Alternatively or additionally, the interface 19 may as well be configured for charging a rechargeable battery for electrical power supply of the evaluation unit 6.

If the sensor 8 is recording pulse rates, as mentioned above, the target state may comprise different statistical variables of the recorded data. An example of this is shown in FIG. 2.

Figure 2:
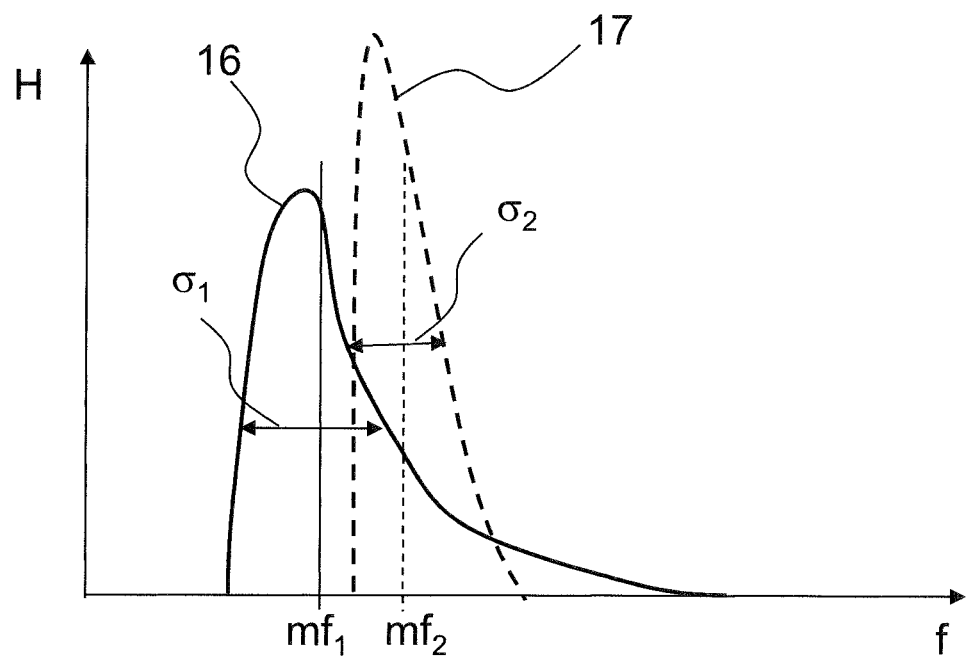
FIG. 2 shows a diagram of a target state and an actual state of an animal as determined using the device.

The embodiment shown in FIG. 2 is generally based on a refinement of the invention according to which the evaluation unit 6 is adapted to compare, on the basis of recorded data from one or more sensors, the frequency distribution of a vital function, in particular the frequency distribution of the pulse rate, with an actual state 17.

In FIG. 2, the pulse rate f is plotted as a function of its frequency of occurrence, that is, the frequency distribution of the pulse rate. A first frequency distribution with a mean value $mf_1$ and a variance $\sigma_1$ represents a target state, the second frequency distribution indicated in dashed lines and having a mean value $mf_2$ and a variance $\sigma_2$ represents a current actual state. At lower rates, the target state distribution 16 measured on the healthy animal has a relatively steep edge since the lower limit of the pulse rate is given by the more or less constant resting pulse. Towards higher rates the frequency distribution decreases more slowly. This shape results from the pulse beat which is increased in varying degrees during activity phases of the animal 2.

The actual state 17 as shown in FIG. 2 indicates that the animal is ill or at least about to become ill. On the one hand, it can be seen that the mean value $mf_2$ is significantly higher than the mean value of the target state $mf_1$. On the other hand, however, the variance $\sigma_2$ of the actual state is smaller than the variance $\sigma_1$ of the target state previously measured and determined on the healthy animal. The lower variance of the actual state indicates that the animal is moving less so that fewer incidents with a high or very high pulse are measured. So the animal 2 obviously has little desire to move. In addition, the shift of the mean value $mf_2$ to higher values indicates a permanently higher resting or base line pulse.

If now one or both deviations of the statistical variables 'mean value' and 'variance' are outside a predetermined tolerance range, then the evaluation unit 6 will signal this to the animal owner. In the example shown in FIG. 1, signaling will accordingly be accomplished by illumination of the light-emitting diodes 100, optionally together with further information on the amount of deviation by varying a flashing rate, color, or brightness.

Figure 3:
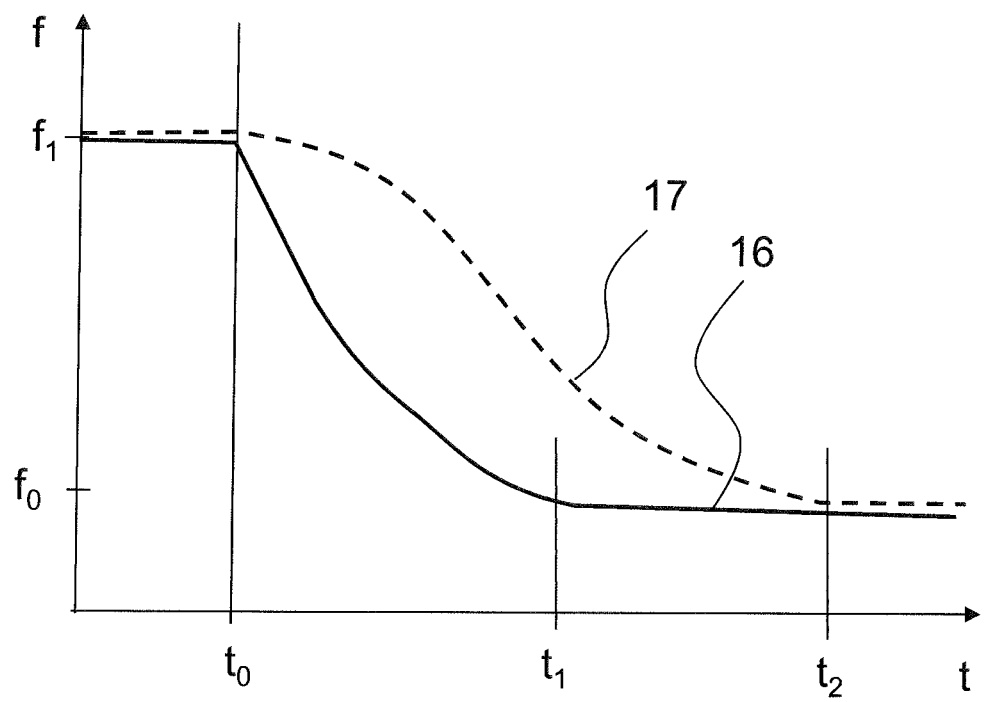
FIG. 3 is a diagram of the measured pulse rate of an animal as a function of time.

FIG. 3 illustrates, by way of a diagram, a further embodiment of the comparison between a target state 16 and an actual state 17 of an animal 2. Without being limited to the particular embodiment illustrated, this embodiment of the invention is based on the fact that the evaluation unit 6 is adapted to determine, on the basis of recorded data and as a parameter of a target state 16, the rate of decrease of the pulse rate as acquired by a pulse rate sensor 80 following a movement phase of the animal 2 as detected by a motion sensor 81 and to compare it with an actual state 17. Therefore, two sensors 8 are provided according to this embodiment of the invention, which detect different vital functions of the animal 2. The two sensors 8 provided for this embodiment of the invention, namely pulse rate sensor 80 on the one hand and motion sensor 81 on the other hand, are also shown in the embodiment of FIG. 1.

FIG. 3 shows the measured pulse rate as a function of time. An end of a movement phase as determined by evaluation unit 6 via motion sensor 81 is at time $t_0$, for both of the profiles plotted in the illustrated example. Due to the physical activity of the animal 2, the pulse is at a high value $f_1$ until time $t_0$. The pulse rate now drops to a value $f_0$ that corresponds to the resting pulse rate. As the parameter of the target state on the healthy/well-being animal the evaluation unit 6 now determines the time interval between time $t_0$ and time $t_1$ from which on the pulse rate remains constant. Here again, an example of an actual state 17 is shown, which is measured later on a diseased or exhausted animal 2. In the curve of the actual state 17, the decrease of the pulse rate to the value $f_0$ takes significantly longer.

According to a preferred embodiment of the invention, the pulse rate sensor is configured as an optical sensor. In this case, a signal emitted by a light source of the sensor 80, reflected and/or transmitted by the animal, is detected by the sensor. This measuring principle is not limited to light in the visible spectral range nor to pulse measurement. Other sensor types are conceivable as well, such as blood oximetry sensors or skin moisture sensors. Therefore, according to a further embodiment of the invention, a sensor 8 for electromagnetic waves is provided which senses a vital function of an animal on the basis of received electromagnetic waves, preferably on the basis of light including infrared and ultraviolet light. In this case there is the further problem that different animals may have different coat colors. Different coat colors absorb electromagnetic waves of different spectral ranges.

It may thus be advantageous to adjust the spectral range of the sensing signal so as to minimize the absorption of the coat. According to an embodiment of the invention it is therefore contemplated that the sensor 8 comprises a radiation source for an electromagnetic sensing signal with a spectral range that is adjustable, for sensing a vital function via the sensor 8. The adjustment of the radiation source with respect to the spectral range of the sensing signal may in particular be accomplished using a control unit which is a component of monitoring device 1, for example in response to inappropriate signal quality. According to an embodiment of the invention, the sensor 8 is an optical sensor and the radiation source comprises a plurality of light sources of different colors, in particular light-emitting diodes of different colors. By switching the light-emitting diodes and thus the spectral range, signal quality can be improved in this manner by avoiding a spectral range with high absorption of the coat. An optical pulse sensor 80 may be mentioned as an example. Green light will produce a good measuring signal for an animal having a white coat in this case. In case of a red or brown coat, absorption of green light might be high due to the melanin contained in the hair. In this case, switching to a red light-emitting diode or additional connection of a red light-emitting diode may be an option. In order to further increase the signal-to-noise ratio, the light source may be operated in pulsed mode, and lock-in technique may be used to filter out the useful signal and to increase its strength relative to the background. Accordingly, in a first refinement of this embodiment the sensor comprises a pulsed radiation source. According to a second refinement, the sensor 8 comprises a lock-in amplifier.

According to a further refinement, the radiation sensor comprises a photodiode operated in dynamic mode, which is initially operated in reverse-biased direction in order to extract free charge carriers. Subsequently, the photodiode is operated in the forward direction, and the time delay until the start of the photodiode current is determined, before the next cycle is started. The current through the photodiode in the forward direction provides a very large signal, which can be easily measured. The change in the time delay until the start of the photodiode current is a measure of the incident radiation.

If in addition to a pulse rate sensor 80 a motion sensor 81 is provided, the evaluation unit 6 will be able to clearly identify a resting phase of the animal 2 via the motion sensor 81. Then, on the basis of recorded data of the sensors, the evaluation unit 6 can furthermore define the resting pulse of the animal 2 as sensed by the pulse rate sensor 80 in a resting phase detected by the motion sensor 81 as a parameter of a target state 16, and can compare it with an actual state 17. An acceleration sensor and/or a gyroscope and/or a step counter may be used as the motion sensor 81, for example.

Additional information that may support the interpretation of the vital data include, for example, environment data such as ambient temperature, which helps in the interpretation of the body temperature or skin temperature as measured using a further temperature sensor. Here, an important application is the indoor temperature in a stable, vehicle, or transport trailer.

Also, sudden changes in additional information, for example ambient noise that is monitored using a microphone as a sensor, may be used for interpreting the pulse rise and/or may trigger the acquisition of additional vital data, such as respiration rate or activity, or of additional information, for example by turning on a monitoring camera.

Figure 4:
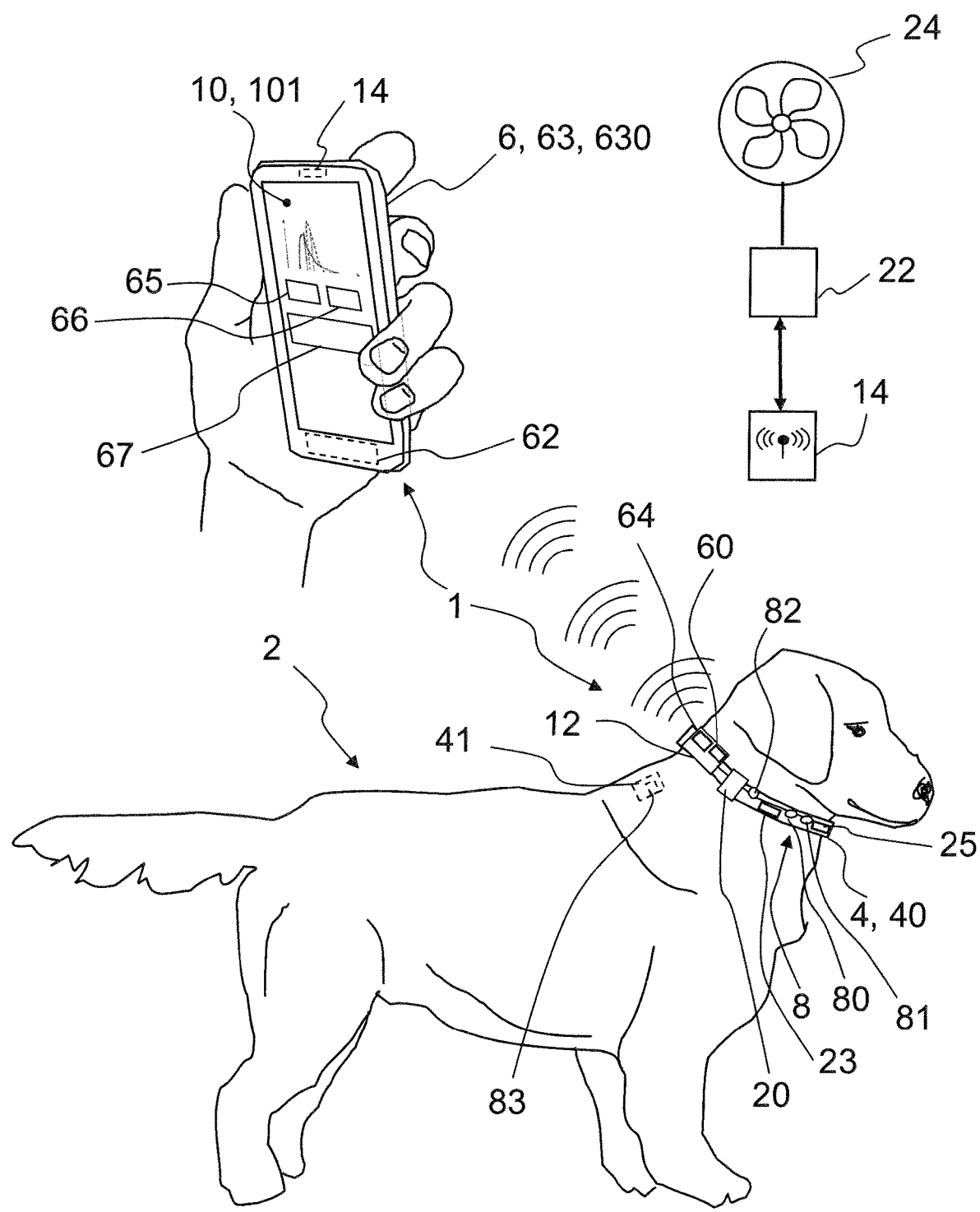
FIG. 4 shows a variant of the embodiment of FIG. 1.

In the embodiment illustrated in FIG. 1, the evaluation unit 6 is integrated in the dog collar 40, so it is attached to the animal via the carrier arrangement 4. However, it is as well possible to partially or completely implement the evaluation unit 6 on an external device. The advantage hereof is, inter alia, that extended options for data evaluation and also for displaying the status of the animal can be implemented in the external device. For transmitting the data from the one or more sensors to the evaluation unit, wireless communication is particularly suitable. Therefore, it is contemplated according to a further embodiment of the invention that the carrier arrangement 4 comprises wireless transmitting means, and that at least a part 63 of the evaluation unit 6 is provided separately from the carrier arrangement 4 and includes wireless receiving means for transmitting data of the at least one sensor 8 from the carrier arrangement 4 to the part 63 of the evaluation unit 6 which is provided separately from the carrier arrangement 4. FIG. 4 shows an embodiment for this case. Like in the example shown in FIG. 1, the carrier arrangement 4 is configured as a dog collar 40. A plurality of sensors 8 for detecting different vital functions of the animal 2 are also provided here. Without being limited to the embodiment, the sensor 8 may as well be a body temperature sensor, or one of a plurality of sensors may be such a body temperature sensor. In the example shown in FIG. 4, a pulse rate sensor 80, a motion sensor 81, and a body temperature sensor 82 are provided. The following sensors are as well possible and advantageous for determining the well-being of the animal on the basis of vital functions:

a respiration rate sensor;
a skin moisture sensor;
an electroencephalographic sensor;
a blood glucose sensor.

The dog collar 40 has a wireless transmitting means 12. The measured values captured by sensors 80, 81, 82 are forwarded to this wireless transmitting means 12 via a cable integrated in the collar 40. The measured values or data corresponding to the measured values are then transmitted by the wireless transmitting means 12.

The part 63 of the evaluation unit 6 which is provided separately from the carrier arrangement 4 may in particular be a mobile device 630, as in the example shown in FIG. 4. Preferably, the mobile device 630 is a smartphone or a tablet PC which is appropriately programmed for evaluation of the data. Mobile device 630 includes wireless receiving means 14 receiving the signals transmitted by wireless transmitting means 12. The received and optionally further processed data are then stored in the memory 62 of mobile device 630. Further processing of the data is then performed by a suitable program of mobile device 630. Accordingly, the program of mobile device 630 accesses the data stored in memory 62 and defines a target state 16 of the vital function of the animal 2 on the basis of the data. Based on data acquired by sensors 80, 81, 82 after the definition of the target state 16 and stored in memory 62, the program determines an actual state 17 and compares the actual state 17 with the target state 16. In the event where a deviation of the actual state 17 from the target state 16 leaves a tolerance range, the program generates an output signal signaling the deviation and outputs it via output unit 10. In case of an external part of the evaluation unit, such as a mobile device 630, in particular a display 101 may serve as the output unit 10. Such a display 101 permits to display the determined deviation in detail and easily comprehensible for the animal owner. As an illustrative example, the diagram of FIG. 2 is shown on the display 101. In this way, the animal owner can easily analyze the deviation of the actual state from the target state, can draw conclusions about the causes and optionally take appropriate measures.

Without being limited to the embodiments, in case of a monitoring device 1 according to a preferred embodiment with a plurality of sensors of different types, the evaluation unit 6 may be adapted for reading the sensors at different sampling rates, depending on the type. This is advantageous, inter alia, since depending on the measured parameter the duration of measurement varies and the variations may also vary. In a movement phase of an animal, for example, an acceleration sensor will output rather fluctuating values, while the pulse rate does not change abruptly. In order to determine a reliable mean value of the activity, a larger number of movement data would have to be averaged than in the case of pulse measurement values. Moreover, energy consumption can be reduced by adjusting the measurement rate or sampling rate.

In the example shown in FIG. 4, the major part of evaluation of the sensor data is performed by the mobile device 630. However, a portion of evaluation unit 6 may as well be attached on the animal 2 using carrier arrangement 4. In the example shown in FIG. 4, signal generator 60 is incorporated in the dog collar 40. Also, it is advantageous to provide a further memory 64 in addition to memory 62. It may advantageously serve as a buffer memory for storing the sensor data at least until they have been transmitted by wireless transmitting means 12 and received by the mobile device 630. This avoids data loss if the wireless communication link between carrier arrangement 4 and mobile device 630 is interrupted.

In the embodiments described so far, the carrier arrangement comprises a carrier arrangement 4 which can be fastened externally on the animal 2, especially a dog collar 40 is provided in the examples. However, if desired, it may as well be advantageous to use an implant housing for arrangement on or under the skin of the animal 2 as the carrier arrangement 4 or part thereof, without being limited to the embodiments. This is for instance useful if the animals hardly get accustomed to the collar. Such an implant housing is moreover suitable for certain sensors which are intended to measure vital functions that can not easily be determined externally.

In the example shown in FIG. 4, an implant housing 41 is provided as a further component of carrier arrangement 4 in addition to the dog collar 40. Implant housing 41 accommodates a blood oxygen sensor 83. It is not compulsory for such a sensor to be arranged in the interior of the body. Blood oxygen may as well be determined through the skin, for example. However, a measurement via a sensor arranged in an implant housing 41 within the body is very precise.

The data of the one or more sensors in implant housing 41 may for instance be transmitted from implant housing 41 to a part of the evaluation unit attached to the body via a wireless interface, in order to be evaluated there, and/or may be further transmitted by wireless transmitting means 12 to a part of the evaluation unit 6 provided separately from the carrier arrangement.

If the signal strength of the signal received by the wireless receiving means is evaluated, information about the location of the animal may furthermore be obtained therefrom. For this purpose, it is contemplated according to an embodiment of the invention that the evaluation unit 6 is adapted for determining a relative position of the carrier arrangement on the basis of the absolute strength of the received signal and its variation over time. Such evaluation allows to determine at least the distance of the animal to the wireless receiving means.

In a further variant, the entirety of the sensors comprises a distributed network of sensors on a carrier arrangement and/or implants and/or of external sensors, which are thus optimally placed at the measurement positions on the animal. Motion sensors on all four legs or hooves of the animal to be monitored, for example, enable to detect movement patterns in detail and to diagnose and display gait errors. Accordingly, a plurality of carrier arrangements might be provided.

Generally, without being limited to the illustrated embodiments, the monitoring device according to a further embodiment of the invention may comprise a feature for determining the period of time from which values measured by the sensor are used to determine the target state. The period can be defined manually by the animal owner. Alternatively or additionally, the period can be predetermined.

Such a feature or function will be referred to as a set function below. According to such an embodiment of the invention, the evaluation unit 6 is adapted to respond to a set signal to define the target state 16 of the vital function of the animal 2 on the basis of the data that have been stored in memory 62 until the time of the set signal. The set signal can be triggered by the evaluation unit 6 itself after a period determined in the evaluation unit, for example after the evaluation unit has been put into operation or after the carrier arrangement 4 has been fastened to the animal 2. Alternatively or additionally, a triggering means may be provided which triggers a set signal when being actuated by the operator of the evaluation unit 6.

In the example shown in FIG. 4, the mobile device is provided with a graphical user interface with a switch button 65 shown on display 101. When the user actuates this button 65, a set signal is triggered which causes the program running on the mobile device to evaluate the data stored in memory 62 in order to determine the target state. Not all the data collected in the past need necessarily be used. Rather, it may be contemplated to evaluate a predetermined time period preceding the trigger time of the set signal, for example a period of one month. Such a set function that can be triggered by the user enables the animal owner to influence the target state by having the target state determined when the animal is in a normal health state or feels comfortable according to the animal owner's impression.

A reset function may be provided as well. Such a function is useful if the status of the animal 2 has changed permanently, for example due to age, so that the previous target state will permanently deviate from the continuously determined actual states.

According to this embodiment of the invention, the evaluation unit 6 is adapted to respond to a reset signal to determine a new target state. For this purpose, data may be collected for a predetermined time period from the triggering of the reset signal, and after expiration of the time period the data stored in memory 62 may be accessed and the new target state can be determined on the basis of these data. In the example shown in FIG. 4, a button 66 for triggering a reset signal is provided for this purpose, similar to button 65.

If the data are stored continuously, the evaluation unit 6 may use the set function as well to determine a new target state by evaluating the data collected within a predetermined period until the time of the set signal and determining a new target state therefrom, when the set signal is triggered. It is likewise possible, upon triggering of the set signal, that one or more previously determined actual states are stored as the current target state.

The determination of a new target state, whether upon triggering of a set or of a reset function, can be helpful in many respects. If, for example, the monitoring device is put into operation on a young animal and the target state is determined, several vital functions will typically change significantly over time until the animal has become adult. Thus, the target state can be reestablished with a respective adaptation to the age of the animal. If the target state of a young animal would be retained for the adult animal, an apparent permanent bradycardia would be determined in the adult animal, for example, since the pulse rate of an adult animal is generally much lower than that of a young animal.

Alternatively or in addition to establishing a new target state in response to a set signal, it is as well possible to concretize an already established target state by continuously taking into account currently measured data for the values of the target state. In other words, according to this embodiment it is contemplated that the target state is updated continuously using data acquired by sensor 8 and stored in memory 62. By taking into account current data, accuracy is increased. For example, the mean value of the pulse and also its distribution function are determined more and more precisely the more values for different measurement conditions are included. It is likewise possible to update the target state by successively precluding older data from being considered. In this way, a gradual natural change in the vital functions, in particular due to maturing or aging, can be easily taken into account.

According to yet another embodiment of the invention, the monitoring device comprises a location determination means for detecting the location of the animal 2. For example a satellite navigation device 20 may be provided for this purpose. Such a location determination means may advantageously supplement or replace the data of a motion sensor 81. The evaluation unit 6 may in fact favorably be configured to determine a movement profile from the position data of the animal 2 read out from the location determination means and stored in memory 62 in combination with the detection times, and/or to determine the activity of the animal. The position data may also be used to distinguish an activity phase from a resting phase, for example, as in the example shown in FIG. 3, and to determine, based thereon, the rate of decrease of the pulse rate as acquired by a pulse rate sensor 80 following a movement phase of the animal 2 detected by the location determination means, and also to determine the resting pulse of the animal 2 as acquired by a pulse rate sensor 80 during a resting phase detected by the location determination means.

The invention is not only useful for detecting disease-related or exhaustion-related deviations from the normal status of an animal 2. The acquired data on vital functions may furthermore provide information about caloric and/or nutrient requirements.

According to an embodiment of the invention, the animal's diet can be controlled on the basis of the measured vital functions, in particular the heart and/or respiration rate and/or body temperature, and optionally on the basis of additional information (such as movement data, age, and weight of the animal, specifications of a veterinarian or animal owner concerning the desired development of the weight or energy supply). For example, the evaluation unit 6 may calculate the required amount of liquid and/or nutrients ("nutrients" in the present sense include carbohydrates, fats, proteins, vitamins, trace elements and minerals, among others) and/or energy (required caloric intake) for achieving a nutritional goal. (Fluid and nutrients are referred to as "food" in the present text).

The evaluation unit 6 may furthermore be adapted to use additional information to monitor the intake of the predetermined food quantities by the animal, for example by (electronically) detecting dispensed food (for example via scanned barcodes on predefined food quantities) and by (electronic) weighing devices or other measuring devices for determining the food intake by the animal.

In a further embodiment of the invention, the necessary food quantities for a certain period of time can be determined from the data about the ingested food quantities, in particular data cumulated over a period of time, and on the basis of the nutritional goal specifications, and can be displayed by electronic/automated notification systems, in particular also by output unit 10, and/or can be purchased via (electronic/automated) ordering systems.

The nutrient content of a portion of packaged food such as dog food (can, dry food) is well-known and is determined easily and accurately even by a lay person (weighing, reading food information via barcode, QR code, et cetera). In a preferred application, the monitoring device is adapted to determine, through precise acquisition of the vital and movement data (for example, pulse measurement and motion sensor) the energy consumption and hence the food requirement or required caloric intake. This analysis or recommendation can be further refined by the evaluation unit by taking into account additional information (breed, outside temperature, veterinary recommendation). Optimized feeding is thus made possible for the lay person in a simple way.

In particular the data of a pulse rate sensor 80 and/or of a motion sensor 81, most preferably a combination thereof, may be evaluated by the evaluation unit 6 according to a further embodiment of the invention for determining the required caloric intake and/or the nutrient requirements and/or liquid requirements. The requirements may be determined and indicated to the animal owner for a predetermined period of time, for example as a daily requirement or else as a current requirement. Accordingly, the evaluation unit 6 may be adapted to determine the requirements of the animal from the data of the at least one sensor 8 stored in the memory 62 as a deviation of the actual state from the target state, and to output the required caloric intake to output unit 10. In the example shown in FIG. 4, the evaluation unit 6 indicates the requirements and/or a corresponding information in a display area 67 for this purpose. Such a corresponding information may for example be a feeding recommendation which might indicate, for example, how much food of one or more types must be fed to meet a determined caloric or nutrient requirement. This embodiment is for instance very helpful in preventing the animal from being permanently over-fed and becoming fat over time or from developing deficiency symptoms. For farm animals, yield can be optimized in this way.

The invention is distinguished by the fact that reliable monitoring of the health state/well-being of an animal is made possible without a priori knowledge about the animal. For example, it is possible to monitor the well-being of a dog without the need for entering specific data such as breed, age, weight, et cetera. However, the invention may of course be further enhanced advantageously if specific information about the animal can be provided. Such information, if available, may be taken into account by the evaluation unit 6 in the evaluation and comparison of the target state with the actual state, or can be displayed together with the result of the comparison. It is likewise possible for the user of an external evaluation unit such as a mobile device 630 as shown in FIG. 4 to compare the result of the comparison of the target state and actual state with relevant additional information. In order to provide additional information to the animal owner and/or the evaluation unit 6, it is contemplated according to a further embodiment of the invention that the monitoring device 1 has an interface for data transmission from or to a database, preferably a portal or an Internet-based user-accessible database, and the data transferable via the interface may comprise at least one of the following contents:

vital function comparison data of other animals;
the current location of the animal;
address data of the animal owner;
data on animal species or animal breed.

The evaluation unit 6 may thus be adapted to retrieve and evaluate relevant data from the database and/or to provide them to the user or animal owner.

Figure 5:
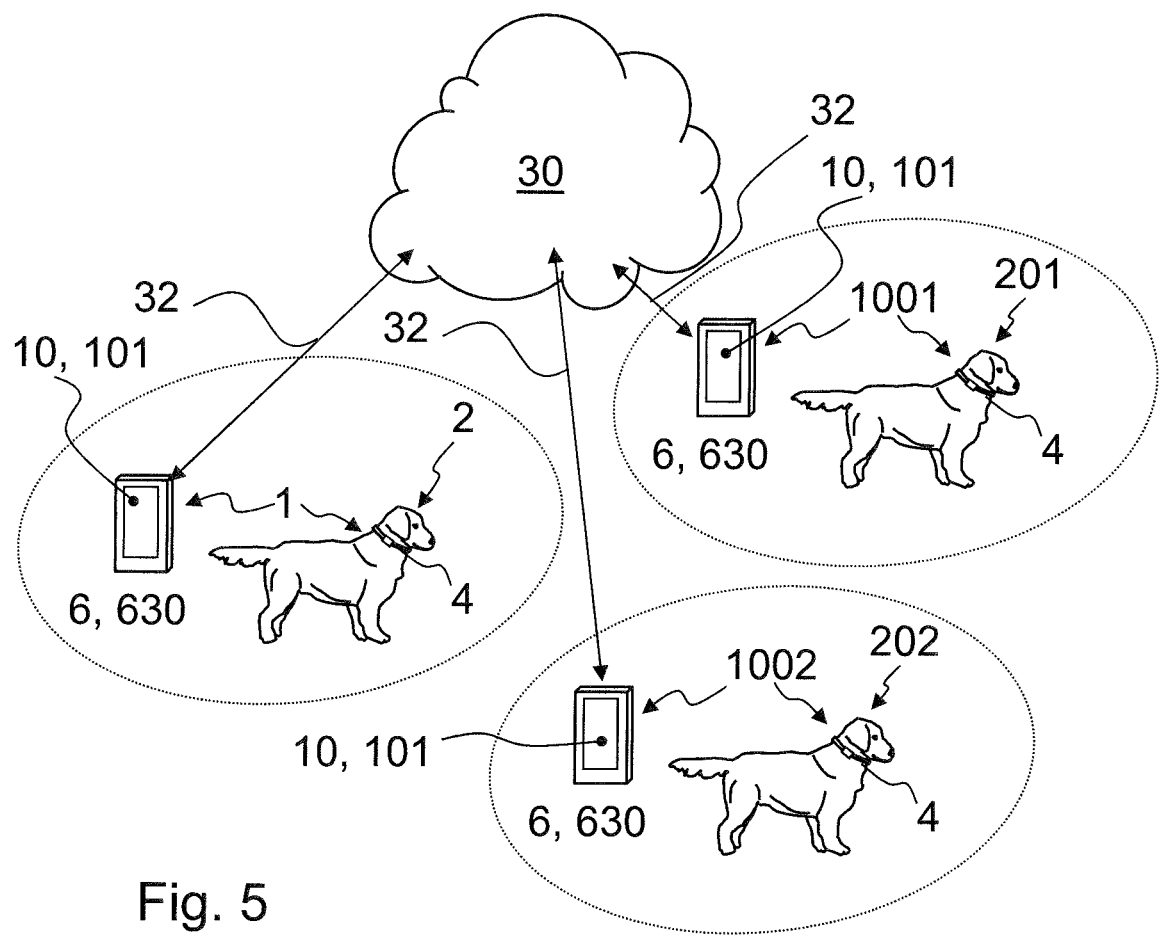
FIG. 5 shows a plurality of monitoring devices in communication with a database.

Particularly preferred is a database in the form of a portal accessible via the Internet. FIG. 5 shows an example for this case. A plurality of animals 2, 201, 202 each are equipped with monitoring devices 1, 1001, 1002 according to the invention. In each case, evaluation units 6 are provided separately from the carrier arrangements 4 of the animals 2, 201, 202. As in the example shown in FIG. 4 it is likewise possible that only a part 63 of the evaluation unit is provided separately from the carrier arrangement 4. More specifically, the evaluation units 6 are configured as mobile devices 630. The evaluation units 6 have interfaces to a database 30. Database 30 may in particular comprise an Internet portal, preferably in the form of a social network. The evaluation units 6 now have interfaces 32 for connection to the database 30. Such an interface 32 may comprise a communication channel for communication of mobile devices with the Internet, for example using GSM.

In the case of a database in the form of a portal accessible via the Internet it is moreover particularly advantageous if the portal is adapted to allow different persons to communicate with each other via the interfaces of the evaluation unit. In this way, the various animal owners may communicate with each other via the database and may exchange data. If the animal owners release address data or position data, such data may then be used by other animal owners to determine whether another animal owner, in particular with a similar animal, is located in reachable vicinity.

It is furthermore particularly advantageous if the animal owners or users of the evaluation unit transmit target states and/or actual states of the animals via the database 30. In this way an animal owner may verify, for example, whether a deviation of the actual state from the target state which is signaled by the output unit 10 (in particular a display 101 of mobile device 630 in FIG. 5) is actually alarming or still within the limits of a normal or acceptable range for the relevant animal breed and the age of the animal.

This embodiment of the invention is therefore based on the idea of collecting data of a plurality of monitoring devices 1 using a database 30 and making them available among each of the monitoring devices 1. Without being limited to the illustrated embodiment, the invention according to a further aspect moreover relates to an arrangement comprising a database 30 and a plurality of monitoring devices 1, 1001, 1002, wherein the monitoring devices 1, 1001, 1002 each have an interface 32 for exchanging data with the database 30, the data comprising measured values of vital functions and/or a determined target state or a determined actual state of an animal 2, 201, 202 wearing the carrier arrangement 4 of the monitoring device 1, 1001, 1002, in particular for comparing a target state or actual state of an animal 2, 201, 202 with the target state or actual state of another animal by the respective evaluation unit 6.

For example, the comparison may be such that the respective evaluation unit 6 is adapted to display the target state or actual state of the animal 2 together with the target state or actual state of another animal 201, 202 as determined from a data set downloaded or retrieved from database 30 by the evaluation unit 6, or
to compare the target state or actual state of the animal 2 with the target state or actual state of another animal 201, 202 as determined from a data set downloaded or retrieved from database 30 by the evaluation unit 6, and to output the comparison result via output unit 10.

The indirect or direct exchange of information from the monitoring devices and/or the carrier arrangement makes it possible, moreover, to supplement and verify the measured data of an animal. For example, not every herd animal needs to wear its own absolute location sensor (for example, GPS sensor) if the relative position of the nearby herd animals is determined by the lead animal or the position marker of the water point, for example.

Also, the upload of the individual measured data into the database may, for example, be accomplished using a GSM modem in a carrier arrangement on the lead animal or using a separately established base station, for example at the water point, so that not every animal needs to wear a GSM modem but collects the data to transmit them upon contact with a "base station".

According to yet another embodiment of the invention, movement data acquired by one or more sensors in the carrier arrangement are calibrated using an external evaluation unit or an evaluation unit provided separately from the carrier arrangement. This calibration or more precise location determination may for instance be achieved using a GPS device in the mobile phone of the animal owner, for example when the dog is taken for a walk. It is also possible to calibrate relative movement data from motion sensors of the carrier arrangement using a location of a WiFi access point that is known more precisely.

However, the output unit is not limited merely to the notification and display of the status or of necessary actions via output to actuators or displays that are directly connected to the carrier arrangement. Rather, with the evaluating unit 6 actions of external actuators as an output unit 10, for example, food dispensers, access controls, or environmental controls may as well be triggered by the monitoring device and/or an output signal thereof, or status indications may be transmitted to external display devices. A common way includes status reports and events in a local network, via Internet or SMS, and notifications in a database or bus system. Generally it will be favorable for the output signal to be transmitted to the receiver in wireless manner.

Generally, without being limited to the illustrated embodiments, the invention accordingly also contemplates an arrangement comprising a monitoring device according to the invention with a wireless transmitting means for transmitting the output signal, and a corresponding wireless receiving means in communication with a control unit, wherein the control unit is adapted to drive at least one actuator in response to the reception of an output signal. The actuator might be, for example, a motor or switch for operating a feeding device. In this way it is possible, for example, to automatically feed the animal appropriately when a required caloric intake is diagnosed by the evaluation unit. A further example is a movement requirement or wake state of the animal, which is determined by the evaluation unit, in particular again by a comparison of the actual state with a target state. In this case, a motor or switch can be actuated by the control unit in response to the reception of the output signal, by means of which an access control in the form of a door or flap is actuated in order to give access to a free-range area, or to switch on an illumination. Another option is a cooling means that is switched on when a stress state of the animal is detected by the monitoring device, which is caused by high temperature. In an embodiment, the vital function 'body temperature' may be compared with the additional information 'external temperature' as determined from an external data source or else internally, for example using an ambient temperature sensor on the carrier arrangement, and an actuator can be driven, such as a shading or cooling means, for example. Possible actuators include, for example, the air-conditioning system in a motor vehicle, or the air-conditioning or shading system in an apartment or a stable. Furthermore, an information may be transmitted to the animal owner as the output signal, for example via a telecommunications device.

In an embodiment of the invention, the monitoring device may furthermore serve as a stress alert or stress detection means, if vital data of the animal do not correlate with additional information, for example if an elevated body temperature does not correlate adequately with movement data and ambient temperature data, or if a high value or increase of the pulse and/or respiration rate does not correlate with the movement data. The evaluation unit 6 may furthermore be configured to discriminate a stress status from an actual state deviating from the target state due to other causes, in particular due to a lack of well-being or illness. For this purpose, additional information may in particular be used, such as acoustic signals recorded using a microphone as the sensor. If the animal is frightened by a loud noise, for example, this can be identified on the basis of the recorded sound signal. The evaluation unit may therefore be adapted, inter alia, to not interpret the increased pulse triggered by the frightening as a deviation from the target state indicating a lack of well-being of the animal.

With respect to further embodiments of the invention as described above, FIG. 4 shows a control unit 22 communicating with a further wireless receiving means 14 which receives the signals transmitted by the wireless transmitting means 12, and an actuator 24 controlled by control unit 22, here in the form of a fan, to provide cooling for the animal in the event of high temperature stress.

In an embodiment of the invention, an actuator is implemented in the carrier arrangement itself. More generally, without being limited to the illustrated example, one or more actuators actuatable by a control unit may be provided in or on the carrier arrangement 4 or as a component of the carrier arrangement 4. Preferably, the control unit is also fastened on or in the carrier arrangement 4. In the examples of FIGS. 1 and 4, control units 23 are provided which drive actuators 25 in the dog collar.

In a preferred embodiment, the actuator 25 can be driven by the control unit 23 to cause the animal's attention, for example, by an air blast, a vibration or acoustic signal which is actively triggered by the animal owner or autonomously when a threshold value is exceeded upon comparison of the target and actual states of a parameter, for example, when a specific radius around a specific person (for example, the animal owner when walking) is exceeded, or when a location is left (for example the garden or the enclosure of the animal owner).

Specifically, this may be implemented by measuring the field strength of the wireless signal (for example, WiFi or Bluetooth) between the collar (carrier arrangement) and the part 63 of the evaluation unit 6 which is provided separately from the carrier arrangement 4, such as a smartphone or other display and control unit of the user. In this manner, the user is alerted when his or her animal goes away and he or she is distracted (jogging with headphones or falling asleep on a chair).

This output may as well be issued to the animal, for example the dog: if the distance exceeds a predetermined value, or if the signal strength drops below a predetermined level, the evaluation unit 6 may be configured to switch on a position light via the control unit 23, or to output a vibration command by a vibration actuator. In this way, a dog can be trained to walk at heel or to come home, for example.

In the example shown in FIG. 4, the monitoring device interacts with devices in the environment, in this case an actuator in the form of a fan. Vice versa, data acquisition and evaluation may however as well take place depending on environmental parameters or external parameters. In particular, the monitoring device 1 may be adapted to perform a comparison of a target state with the actual state in dependence of a preferably not time-dependent or at least not directly time-dependent external parameter. This may in particular include not only a single comparison but also the frequency of comparison or, otherwise stated, the time interval between comparisons. An external parameter is a parameter which does not refer to a vital function of the animal. However, such a parameter may relate to the vital function(s) of other animals. Accordingly, an external parameter is a measured variable relating to the environment, including persons such as the user or owner of the animal. Such a parameter can be, for example, the absolute position, the distance of the animal to further animals, the distance to the animal owner or to an external evaluation unit, the outside temperature. For example, if a plurality of animals of a herd are equipped with monitoring devices 1 according to the invention and if a monitoring device 1 of one of the animals detects a greater distance from the other animals, this could indicate that the animal in question is sick or injured. Likewise, the current spatial distance to the reference person such as the animal owner may be due to an injury. Comparison data can also comprise the values of vital functions of other herd animals such as the actual average pulse, or the current average temperature. Thus, the deviation of the external parameter from a target range or from a usual value may be a useful good hint for verifying the health state or the well-being of the animal. Therefore, according to a further embodiment of the invention the monitoring device 1 is adapted to perform a comparison of the target state with the actual state in response to an external parameter.

It will be apparent to those skilled in the art that the invention is not limited to the embodiments described above with reference to the figures, but that the features of the individual embodiments can be combined with one another. For example, it is conceivable that communication with a database 30 as in the example shown in FIG. 5 may take place with an evaluation unit 6 integrated in the carrier arrangement 4 without need for a user of a part 63 of the evaluation unit 6 provided separately from the carrier arrangement 4 to control or initiate the querying of the database 30. Furthermore, in the figures the invention is illustrated only by way of carrier arrangement in the form of dog collars 40 and implant housings 41. However, carrier arrangements for other animals, such as for cats or horses and for farm animals are of course also possible.

Furthermore, it is also suggested that not only the evaluation unit 6 of the monitoring devices 1, 1001, 1002 have access to the data of database 30, but also other persons. A useful option would be to enable a veterinarian to access the database via the Internet. In this way, the animal owner can easily consult the veterinarian and the veterinarian may optionally make a diagnosis on the basis of the vital function data stored in the database, or may at least give a recommendation as to whether a doctor's visit is necessary.

Furthermore, as described above with reference to FIG. 1, the electronics of the evaluation unit 6 in carrier arrangement 4 can be powered by a rechargeable battery which can be charged via an interface 19. Alternative or additional devices for power supply and/or for charging a rechargeable battery are also possible. For example, an energy harvesting device may be provided which gains electrical energy from the movements of the animal, for example, and/or which comprises a photovoltaic cell. If the energy is generated from the movements of the animal, it is furthermore possible according to an advantageous further embodiment of the invention that the device for harvesting movement energy or for generating electrical energy from movements of the animal which charges an electrical energy storage of the carrier arrangement is simultaneously used as the sensor 8, since in this case the gained energy corresponds to the activity of the animal. Accordingly, the monitoring device may be adapted to store in memory 62 or directly read data corresponding to the gained energy, and in this case the evaluation unit will accordingly be adapted to read out these data corresponding to the gained energy and to evaluate them to determine an actual or target state. Data corresponding to the gained energy which may be evaluated include the charging state of the energy storage in the carrier arrangement, inter alia.

According to yet another embodiment, a motion-induced power generation device, that means a device for generating electrical energy from movements of the animal, may be implemented in the carrier arrangement in addition to the power supply unit or the energy storage as in the embodiment described above, which in addition to power generation purposes can be used, in a function reversal, as an actuator for generating attention (for example for generating a vibrational pulse), and/or, by measuring the charging state of the power supply unit, as a measuring instrument for the total of movements exerted by the animal (integrating motion sensor). More generally, without being limited to the illustrated examples, a device for generating electrical energy from movements of the animal may therefore be provided, which may be operated as an actuator for emitting a vibration signal to the animal, by supplying electrical energy, using a control unit 23 that may in particular be a component of the evaluation unit 6. Advantageously but not necessarily, the device for generating electrical energy may as well be used as a sensor in this case.

In the embodiments of the invention described so far, a deviation of a status from a tolerance range was used as the basis for outputting an output signal. Vice versa, however, it is also possible to output, via output unit 10, an output signal in the event of a correspondence between an actual state and a target state, in particular an output signal which indicates the correspondence.

By continuously measuring signals using the one or more sensors of the carrier arrangement it is possible to determine behavior profiles (defined as 'behavior' or 'gestures') which represent recurring or typical behavior (of the individual animal or in its animal group) and which allow an evaluation of the status and also conclusions about the condition and well-being of the animal. For example it is possible to create movement profiles on the basis of individual movements.

More generally, without being limited to the illustrated and described embodiments, it is therefore contemplated according to an embodiment of the invention that the evaluation unit 6 is adapted to access the data measured and stored in memory 62, and to determine, on the basis of these data, at least one target state 16 of a behavior pattern, and to determine an actual state 17 on the basis of the data acquired by the sensor 8 after the definition of the target state 16 and stored in the memory 62, and to compare the actual state 17 of the behavior with the target state 16 that represents a behavior pattern, and preferably, in case of a correspondence between the actual state 17 and the target state 16, to output an output signal. Alternatively or additionally to the emission of an output signal, the event of correspondence may as well be stored in memory 62. These matches can now be evaluated for determining another target state for monitoring the well-being of the animal by the evaluation unit 6. One example would be an elimination behavior pattern of the animal. As a further target state it could then be evaluated when and how often the animal relieves itself on average. If hereinafter, as a result of the comparison of behavior patterns, the evaluation unit 6 detects significant deviations from these mean values, that is, deviations leaving a tolerance range, this will be signaled by the output signal. Frequent elimination would indicate a diarrheal disease, for example, the opposite case constipation.

Figure 6:
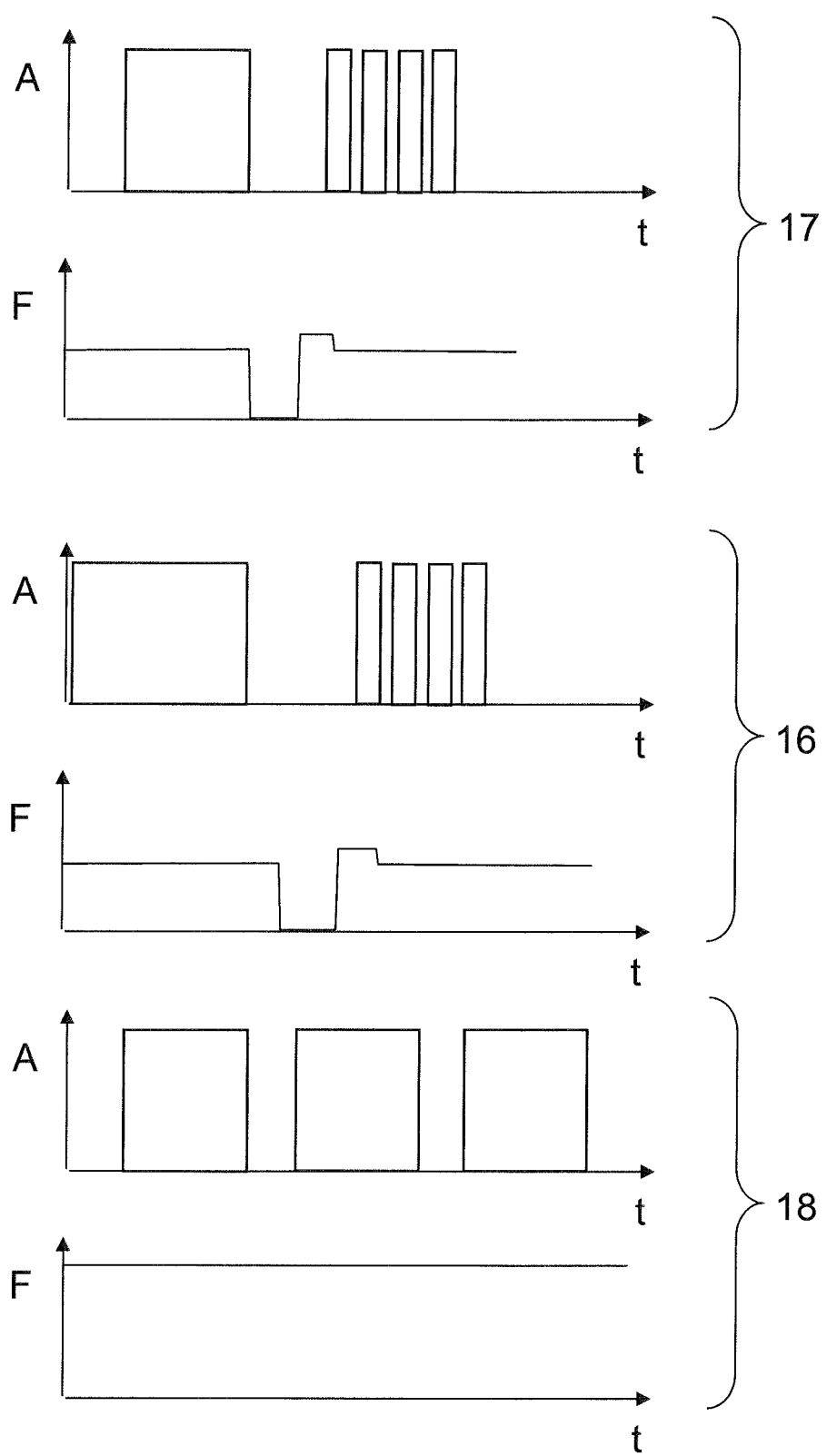
FIG. 6 schematically shows a comparison of recorded sensor data representing behavior patterns of an animal.

An example for the comparison of behavior patterns is shown in FIG. 6. The actual state 17 is compared with two target states 16, 18, which represent behavior patterns. Each status 16, 17, 18 comprises a combination of two time sequences. The upper diagram represents the short-term profile of an activity A of the animal, in particular as measured with a motion sensor. This profile is correlated with the variation of respiration rate F over time. The actual state 17 schematically shows a behavior pattern when an animal, for example a dog, eliminates. First, the animal is in a more or less uniform motion, then stops, which can be seen from the abrupt drop in activity, then paws the ground. The pawing produces a typical movement pattern with short periodic activity peaks. During eliminating the dog stops respiration briefly, followed by a short phase with faster respiration, which can be seen from the respiration rate profile over time.

Memory 62 of evaluation unit 6 now stores a plurality of behavior patterns 16, 18 which are compared with the currently measured data. The comparison shows the similarity of the actual state with behavior pattern 16, while target state 18 shows a different characteristic of both the movement curve and the respiration rate curve. Evaluation unit 6 will identify the conformity of states 16, 17 and can then signal, by issuing an output signal, that the dog has eliminated. Alternatively or additionally, the event of eliminating may be recorded and compared with a further target state with respect to other criteria such as the frequency of the event.

In combination with a location measurement protocol or with a location determination device for detecting the position of the animal 2, the monitoring device may furthermore advantageously be configured to display the location of elimination, that is, the location of the animal's droppings. This permits, for example, to find and remove a dog's droppings which was "eliminated" in an unobserved moment. In order to train the evaluation unit 6 for specific behavior patterns, a set signal can be triggered by the user in an advantageous embodiment. For example, when the animal owner sees that the animal eliminates, the animal owner may trigger the signal so that the behavior pattern is stored. According to this embodiment of the invention it is therefore contemplated that the evaluation unit 6 is adapted to respond to a set signal to determine, for a behavior pattern of the animal 2, the target state 16, 18 of the behavior pattern on the basis of the data that have been stored in the memory 62 until the time of the set signal.

Other behavior patterns or applications include the behavior in the event of flatulence, which is very important in keeping horses, identifying a cover (active or passive), hunting attempts, barking at persons, births, bending the neck in farm animals (horse, cow), and swallowing movements while browsing. In this case, the quantity of food over time and/or the number of swallowing movements can be estimated, for example. Thus, a horse can be fetched from the pasture before a specific quantity of green grass is exceeded in order to avoid the animal becoming sick. The quantity of supplementary feeding may also be optimized in this way. Another behavior pattern which can be identified by sensors and which is significant for caring and nurturing is vomiting of the animal.

In an embodiment, the invention moreover serves to log and/or interpret the mutual contacts of animals wearing the device according to the invention, for example the duration, frequency and quality (on the basis of the behavior patterns described above) of the contacts of animals within a herd and the variation of vital functions, for example, heart and respiration rate. Where appropriate, additional data such as movement or location data may be combined in order to keep records of social hierarchies in a herd or cover attempts, for example.

The invention may furthermore be used to draw conclusions about the quality of care and/or the reliability and activity of the animal keeper, through acquisition of specific data of the animal such as movement profile, feeding times. For example, if the animal is accommodated externally, compliance with the feeding and movement times that are required for the individual well-being (comparison target/actual) can be monitored. If the animal is a companion of elderly family members, it is possible to ascertain whether this person is mobile and "healthy", for example whether the elderly person that lives alone regularly feeds the dog according to its individual parameters of well-being and takes it for a walk or whether he or she does not leave the house for an extended period of time.

Not only natural movement sequences can be classified and identified by a spatially remote owner using the monitoring device according to the invention, trained behavior can also be verified by such "gestures". For example pawing, "sit", "down", "roll over", "speak", or even more complex behavior can be trained and can be evaluated even for spatially remote animals using the monitoring device. An advantageous application is resulting in this way for search and detection dogs when deployed without direct guide, for example, in particular in the case of unclear and dangerous situations in catastrophe or combat areas (for example in an avalanche area or mine field).

Often, it is not easy or uncertain without a priori knowledge to classify a pattern of vital functions as a normal condition suitable for the target state. For example, it may already be difficult to associate behavior patterns on the basis of specific sensor data such as shown in FIG. 6. The set function already described before can be used very advantageously for this purpose. If the monitoring device 1 stores the measured values and the animal owner detects that the animal exhibits a certain status, such as a certain behavior pattern or movement pattern, the animal owner can qualify a specific pattern of sensor data to define a status of the animal through association by triggering a set function. In order to keep the sensor data available for a qualification of the state such as a certain behavior or movement pattern, for example, it is contemplated according to an embodiment of the invention that the monitoring device 1 is adapted to continuously buffer sensor data and, for at least a portion of this data and in response to a set signal that can be triggered by a user, to associate them to a user-definable status of the animal.

The specific association may as well be made later. According to one variant, sensor data associated with the time of the set signal are marked for this purpose in response to a set signal which can be triggered by the user of the evaluation unit. The user can then associate the marked data with a status of the animal as described above at a later time, preferably via a graphical user interface.

The status may for instance be selectable via a menu of a graphical user interface. If desired, the user may as well enter a description of a status, preferably via an input mask of a graphical user interface, and the sensor data may then be associated to the entered status description in response to a set signal. According to a further refinement of this embodiment of the invention, the marking of the data furthermore prevents the data from being erased from the buffer.

Generally, the memory 62 need not be different from the buffer or cache. For example, a portion of memory 62 may be used as a buffer or cache memory, or the memory 62 is spatially divided, with one spatially separated portion functioning as a cache memory.

If, for example, the animal owner notices a particular behavior of the animal, which has not yet been taken into account in the target state, the above-described procedure can be used to supplement the target state. To mention an example, the animal owner might observe his dog swimming. The animal owner may now trigger the set function on his mobile device 630 to set a time mark. For example, the sensor data acquired in the last two minutes are marked in this case. Subsequently, the animal owner can then associate an event or a status to the marked data using his mobile device. If the status, "animal is swimming" in the present case, is already provided for selection, this status can be selected and so be associated with the sensor data. The status may as well be directly associated according to the other alternative described above. If the animal owner is watching the animal swimming, he or she can directly select or enter the status "animal is swimming". The association of the sensor data to the selected status is then made in response to the selection by the user.

A particular advantage of the embodiment of the invention in which, more generally stated, data are associated with a status or behavior of the animal or with an event by a set signal is that the target state can be individually extended by data sets that characterize certain states of the animal. According to a further embodiment, this extension can be controlled by an interaction with the user. For example, after association of the sensor data the evaluation unit may request of the user whether the target state shall be extended by this status. If the status is recorded from time to time, the evaluation unit may then later identify a deviation from the extended target state. With respect to the example of the swimming dog, the monitoring device might identify an excessive decrease in the body temperature during repeated swimming of the dog and can alert the animal owner via output unit 10.

More generally, without being limited to the embodiments, it may therefore be contemplated according to a further embodiment of the invention that the evaluation unit is adapted to supplement the target state by states which are characterized by the sensor data associated by the user.

Furthermore, a device may be provided which allows the user of monitoring device 1 to qualify actual states, supplemented states, or marked data. Such a qualification may describe the behavior and the status of the animal with attributes that can not be derived from a measurement of a deviation of the actual state from the target state without a priori knowledge. In particular characterizing attributes or adjectives such as "anxious", "cheerful", et cetera can be entered. This qualification entered by the user may then be stored as part of a status of the animal or of a deviation of the actual state from the target state. If a similar deviation occurs again at a later point in time, the monitoring device will be able to recognize this status and can signal this to the user via output unit 10. In this way, the monitoring device according to the invention can even learn to identify the animal's state of mind. Thus, according to an embodiment of the invention an input device of the monitoring device 1 is provided, which can be used to enter and add to the stored data an attribute that describes the behavior or the status of the animal. The evaluation unit may then furthermore be adapted, on the basis of a comparison with the stored data, to associate an actual state with the attribute, and to output the attribute via output unit 10 in case of a sufficient correspondence.

According to yet another embodiment of the invention the evaluation unit may be adapted to supplement the target state by absolute threshold values entered by the user. Such an addition is advantageous, inter alia, if the animal is under medical treatment or surveillance. For example, a maximum pulse or a maximum body temperature may be specified for this purpose.

Figure 7:
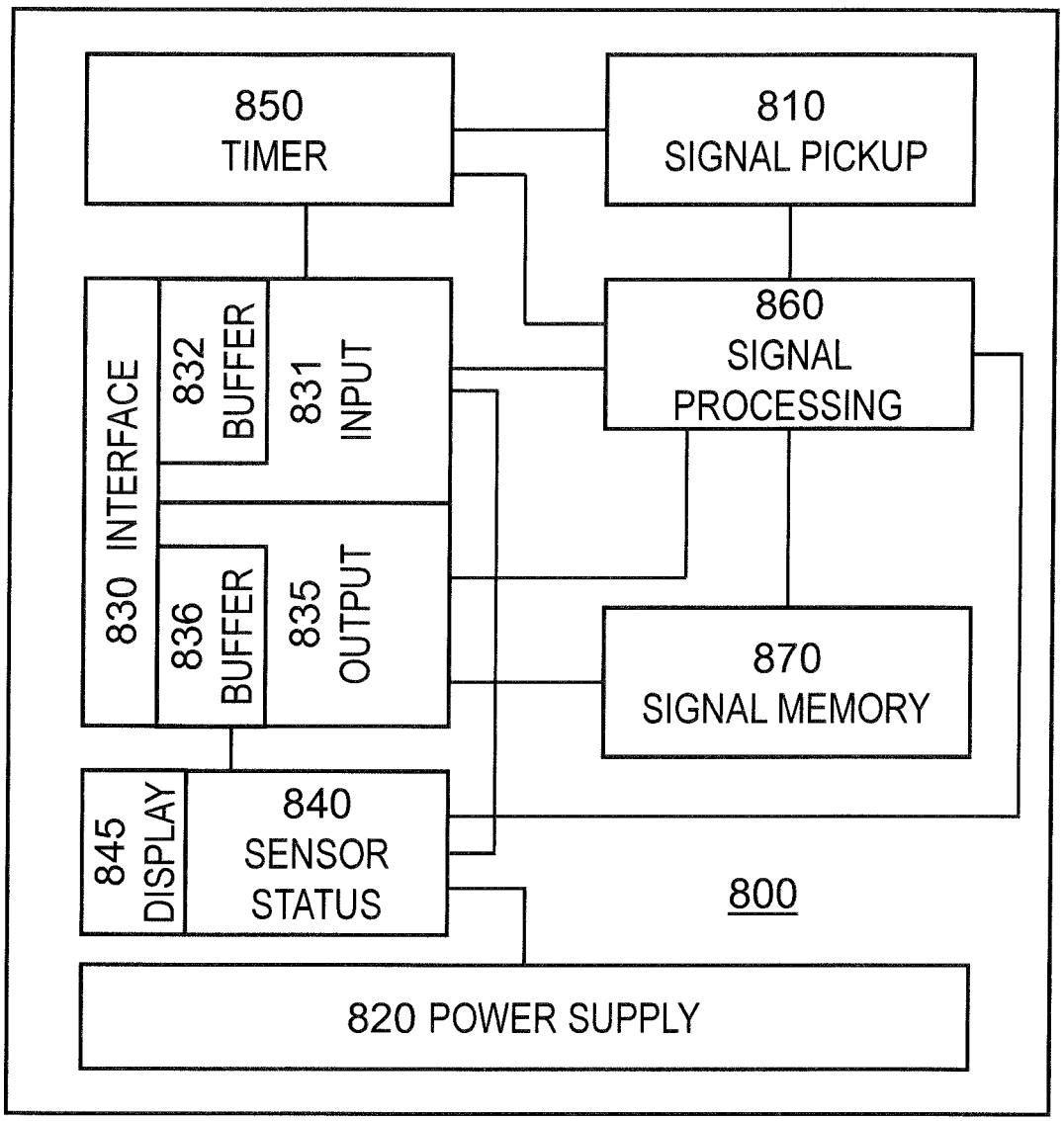
FIG. 7 shows the configuration of a sensor node.

In a preferred embodiment of the invention, one or more sensors 8 of monitoring device 1 are configured as autonomous sensor nodes 800 which are at least temporarily connected to a network of sensors that is preferably controlled by an evaluation unit. FIG. 7 illustrates a corresponding autonomous sensor node 800 by way of example.

Figure 8:
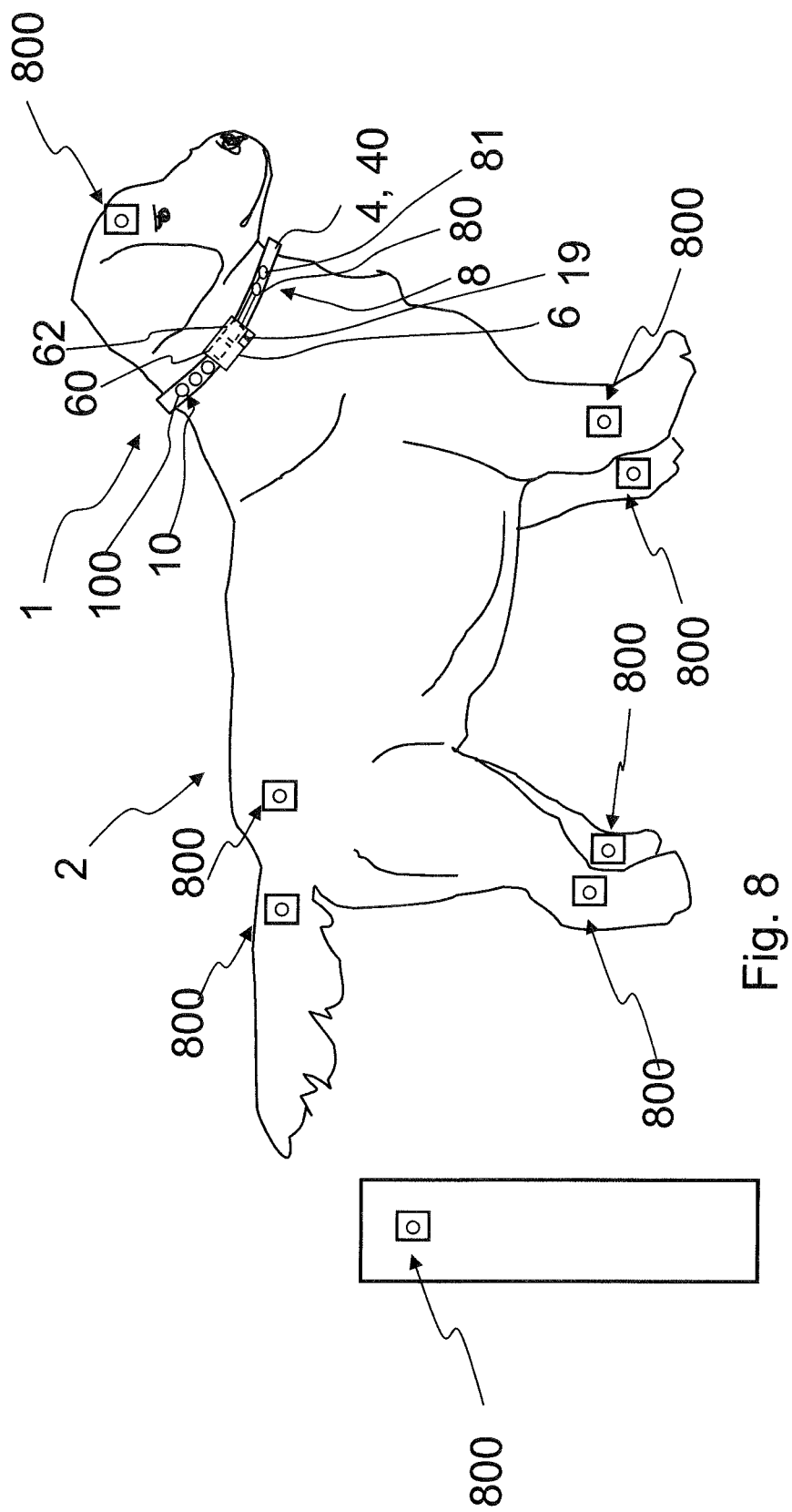
FIG. 8 shows an animal with a monitoring device comprising a plurality of sensor nodes 800.

FIG. 8 shows, as a variant of FIG. 1, an embodiment of the monitoring device 1 according to the invention with a plurality of spatially separated sensor nodes 800. The idea hereof is that the individual sensor nodes 800 form network nodes for exchanging information. This provides a flexible possibility for distributing the sensor nodes on the animal and optionally also on an external measuring or monitoring device.

This embodiment of the monitoring device 1 for monitoring vital functions is based on the fact that at least one sensor 8 is in the form of an autonomous sensor node 800 that is attachable on an animal 2 for detecting a vital function, the sensor node 800 comprising
  at least one signal pickup 810,
  at least one autonomous and/or central power supply 820,
  at least one analogue and/or digital interface 830, and
  at least one analogue and/or digital timer 850,
wherein the sensor node 800 is further adapted to be at least temporarily connected to a wired and/or wireless and/or optical network with an evaluation unit 6 that is preferably attachable to the animal 2 separately from the sensor node 800 and/or with at least one further autonomous sensor node 800 that is attachable to the animal 2 separately from the sensor node 800. Here, the term "autonomous" in particular means that the sensor node is independent of an evaluation unit 6 with regard to the attachment on the animal and/or the power supply. The sensor node can thus be separately attached to the animal and/or has its own separate power supply.

The autonomous sensor node 800 has at least one active and/or passive signal pickup 810. Active signal pickup refers to a signal pick-up including an excitation/receiving means. An active signal pickup in the form of an optical pulse meter 80, for example, comprises an excitation means in the form of a light-emitting diode that emits a light signal which is received by a receiving means, for example in the form of a photodiode, and has undergone measurable modulation due to the pulse of the animal. A passive signal pickup has no excitation means. An example of a passive signal pickup is a temperature-dependent resistor for temperature measurement.

According to an embodiment, the sensor node 800 furthermore has an autonomous and/or central power supply 820. In the simplest case, the sensor node is powered via supply lines from a central energy storage, for example from the energy storage of the evaluation unit. These supply lines may as well comprise the inductive coupling for energy transmission, for example according to the Qi standard, which can be used particularly advantageously at the attachment interfaces of the sensor node. Particularly advantageous is the configuration with an autonomous power supply, in which case the sensor node has its own power supply, for example a rechargeable or other battery, which may be supported by energy harvesting and/or by renewable energy, for example, by solar cells. Fast charging of the energy storage means of the sensor node may be promoted via non-permanently connected power supply lines, in particular also by inductively coupled connections. Advantageously, the power supply is configured to be highly energy saving and is able to power individual units of the sensor node separately from one another and/or to control switching to energy-saving operating states. For example, the communication with the evaluation unit can be powered and maintained via interface 830, while the active signal generator 810 of the optical pulse measurement with its energy-consuming light source remains switched off and/or signal processing 860 remains in a deep-sleep mode.

Furthermore, the sensor node has at least one analog and/or digital interface 830 for inputs 831 and outputs 835 to and from the network of sensors. The embodiment in the form of an analog interface, for example, comprises the output via at least one signal line and/or the start of a measurement via a trigger line. The digital interface comprises wired communication via control and/or address lines. The use of a bus system such as I2C, for example, is advantageous. Particularly advantageous is an embodiment including the digital interface in the form of a wireless interface, by using Bluetooth, Bluetooth LE, WiFi, or GSM, or as an optical data bus. The interface allows, for example, to transmit parameters, measured values, data, programs, and/or status information, and to synchronize, trigger, and/or stop actions and/or measurements. The inputs and outputs via the interface may be buffered. Buffering 832, 836 allows for an asynchronous operation of the sensor nodes and is particularly advantageous if sensor nodes are connected to the network only temporarily or might drop out of the network due to temporary disruptions, and supports the complete transmission of the data. The buffer memory of the interface may be implemented both as an analog or digital memory. For example "sample and hold" circuits are used as an analog buffer. The digital buffer memory may comprise volatile and/or non-volatile memory means. One-time programmable memory is particularly suitable for storing identifiers, serial numbers, and invariable parameters. In a particularly advantageous embodiment, the interface 830 triggers the waking-up of the sensor node from an energy-saving deep sleep and initiates a measurement, then provides the determined data, and then returns the sensor node back into the energy-saving operating state after the data have been read out.

The sensor node may have a sensor status unit 840 which provides and outputs information about the state of the sensor via a discrete and/or digital display 845. The discrete display may, for example, be implemented using LEDs and/or a display which for instance indicates the operating state of the sensor, displays the signal quality during a pulse measurement and thus also helps in placing the sensor at a specific position, indicates the charging state of the power supply, and/or informs about the connectivity of the interface, for example the pairing status of the Bluetooth connection to the evaluation unit, and/or may display the last measured value directly at the sensor without need to use the display unit of the evaluation unit. The information about the sensor status may as well be provided via interface 835 with 836, in particular as a digital information. Furthermore, the sensor status 840 and its indication may be programmed or controlled via interface 831 with 832. This advantageously allows, for example, to name and configure the sensor node, to assign an address in the network, to help in arranging the sensor at an appropriate point and in optimization of the signal quality, indication of the sensor name and/or the animal, of the position for fastening, and/or guidance for signal optimization.

An integrated timer 850 may preferably determine the time and the time intervals of the measurements and/or provide a time stamp for the measurements. For example, it may synchronize and/or start the measurements via the interface 830 and/or support continuous autonomous measurements. In a particularly advantageous embodiment, the timer allows and/or controls the switching of the sensor node to different operating states, such as, for example, the waking-up from a deep sleep mode for energy saving purposes. According to a further embodiment of the invention, the integrated timer 850 may as well be configured to read out the signal pickup at different time intervals depending on the type of the signal or signal pickup.

The autonomous sensor node may comprise analog and/or digital signal processing 860. Analog signal processing comprises, for example, one or more amplifiers and/or impedance converters, correlators, integrators, and/or filters, such as, for example, suppression of the direct current component of the photocurrent in case of optical pulse measurement. Digital signal processing comprises, for example, a programmable microcontroller, analog-to-digital conversion, determination of the mean value and/or of the determination of the measured values, mathematical methods and transformations (for example, fast Fourier transformation), autocorrelation with stored data and/or data sequences, integration, derivation, and/or curve fitting. Parameters, models, and programs of signal processing 860 can be updated, programmed and/or retrieved via interface 830. Data and data patterns can be temporarily stored in signal memory 870.

The autonomous sensor node may comprise an analog and/or digital signal memory 870. The analog signal memory may, for example, comprise a sample-and-hold circuit and provide the measured value until a new measured value has been determined. In a further advantageous embodiment, the signal memory is digital and comprises volatile and non-volatile digital memories. Thus, current measured data and results may be temporarily stored in a RAM prior to, during, and/or after processing by signal processing means 860. Measurement parameters, pattern sequences for gesture recognition, programs, and control information can be provided and stored in flash memories even over a long period and independently of the power supply. Security-relevant and/or sensitive data may as well be encrypted.

A simple attachment to the animal is of particular advantage for the sensor node 800 in order to allow for attachment on the animal in different places depending on requirement and type of the sensor. For example, it may be desirable to provide an acceleration sensor on the tail or on the legs in order to detect specific activity patterns. For animals which have hair or feathers, attachment means with barbed hooks that anchor in the hair or feathers are particularly suitable. For animals without hairs or feathers, a fastening device with adhesive anchoring may be used.

It is understood that the foregoing description is that of the preferred embodiments of the invention and that various changes and modifications may be made thereto without departing from the spirit and scope of the invention as defined in the appended claims.

LIST OF REFERENCE NUMERALS:

1, 1001, 1002 Monitoring device
2, 201, 202 Animal
4 Carrier arrangement
6 Evaluation unit
8 Sensor
10 Output unit
12 Wireless transmitting means
14 Wireless receiving means
16, 18 Target state
17 Actual state
19 Interface
20 Satellite navigation device
22, 23 Control unit
24, 25 Actuator
30 Database
32 Interface to 30
40 Dog collar
41 Implant housing
60 Signal generator
62, 64 Memory or data storage unit
63 Part of evaluation unit 6 provided separately from carrier arrangement 4
65 Set switch button
66 Reset switch button
67 Display area for required caloric intake
80 Pulse rate sensor
81 Motion sensor
82 Body temperature sensor
83 Blood oxygen sensor
100 Light emitting diode
101 Display
630 Mobile device
800 Sensor node
810 signal pickup
820 power supply
830 interface
831 input
832 input buffer memory
835 output
836 output buffer memory
840 sensor status
845 display
850 timer
860 signal processing
870 signal memory

What is claimed is:

1. A monitoring device for monitoring vital functions, the monitoring device comprising:
at least one carrier configured to be attachable to an animal and including at least one sensor configured to sense a vital function of the animal wearing said carrier, and an evaluation unit configured to communicate with said at least one sensor; and,
an output configured to output an output signal;
wherein said evaluation unit further comprises a signal generator and a data storage unit;
wherein said signal generator is configured to emit signals at time intervals; and,
wherein said evaluation unit is configured to store at least one sensed value of a vital function sensed by said sensor in response to a signal from said signal generator and to store said at least one sensed value in said data storage unit and to add at least one of a data item corresponding to said at least one sensed value to said data storage unit;
wherein said evaluation unit is furthermore configured to access stored sensor data in said data storage unit and to autonomously define a target state based on said accessed stored data including a target state of the vital function of the animal including a target state of at least one of a pulse rate; a body temperature; a blood oxygen; a respiration rate;
the target state being indicative for a normal health state of the animal; and,
to determine an actual state on the basis of the data sensed after the definition of the target state and stored in said data storage unit, the actual state including at least one of a pulse rate; a body temperature; a blood oxygen; a respiration rate; and to compare the actual state with the target state; and
in case of a deviation of the actual state from the target state or in case of a correspondence between the actual state and the target state, to output an output signal via the output including an output signal which signals the deviation or correspondence, wherein the evaluation unit is configured to respond to a set signal to define said target state of a behavior pattern of the animal on the basis of data stored in said data storage unit until a time of the set signal, or to continuously update the target state using data sensed by said sensor and stored in said data storage unit,
the monitoring device further comprising a trigger actuatable by an operator which triggers the set signal when being actuated by the operator of the evaluation unit.

2. The monitoring device of claim 1, comprising at least one of the following sensors: a pulse rate sensor; a motion sensor for detecting movements of the animal; an acceleration sensor;
a gyroscope; a step counter; a body temperature sensor; a blood oxygen sensor; a respiration rate sensor; a skin moisture sensor;
an electroencephalographic sensor; a blood glucose sensor; and
a device for generating electrical energy from movements of the animal.

3. The monitoring device of claim 1, wherein the carrier comprises at least one of the following: an animal collar; a dog collar; a harness; a halter; and, an implant housing for being placed on or under the skin of the animal.

4. The monitoring device of claim 1, wherein the evaluation unit is configured to statistically evaluate data stored in the data storage unit and to determine said target state on the basis of at least one statistical parameter obtained from the evaluation.

5. The monitoring device of claim 1, wherein the evaluation unit is configured to determine at least one of the following parameters of said target state on the basis of recorded data of one or more sensors and to compare them with said actual state:
a frequency distribution of a vital function including the frequency distribution of the pulse rate;
a rate of decrease of the pulse rate as acquired by a pulse rate sensor following a movement phase of the animal detected by an acceleration sensor; and
a resting pulse of the animal acquired by a pulse rate sensor in a resting phase detected by the motion sensor.

6. The monitoring device of claim 1, wherein the evaluation unit is configured to access sensed data stored in said data storage unit and to determine, on the basis of said data, at least one target state of a behavior pattern, and to determine an actual state on the basis of the data sensed by said sensor after the definition of said target state and stored in said data storage unit, and to compare said actual state of the behavior with said target states of the behavior pattern.

7. The monitoring device of claim 1, wherein said carrier comprises a wireless transmitter; and wherein at least one part of said evaluation unit is provided separately from said carrier and includes a wireless receiver for transferring data of said at least one sensor from said carrier to the part of said evaluation unit which is provided separately from said carrier.

8. The monitoring device of claim 7, wherein the evaluation unit is configured to determine a relative position of the carrier on the basis of an absolute strength of the received signal and its variation over time.

9. The monitoring device of claim 1, wherein the monitoring device is configured to continuously store sensor data and, for at least a portion of this data,
- to associate them to a user-definable status or to a user-definable attribute of the animal in response to a set signal of said trigger in a form of a switch button that is triggered by a user of the evaluation unit; or
- to mark sensor data associated with a time determined for triggering the set signal of said trigger.

10. The monitoring device of claim 1, wherein an input is provided which can be used to input an attribute for said data storage unit, which describes the behavior or condition of the animal.

11. The monitoring device of claim 1, wherein the evaluation unit is adapted to determine, on the basis of the data of the at least one sensor stored in said data storage unit as a deviation of the actual state from the target state, a required caloric intake or food requirements of the animal, and to output the required caloric intake or food requirements to the output.

12. The monitoring device of claim 1, comprising a location determiner configured to sense a location of the animal comprising a satellite navigation device.

13. The monitoring device of claim 1, wherein said evaluation unit is configured to sense further data from at least one external data source in addition to the data sensed by said at least one sensor, and to take said external data on the basis of at least one data when comparing said target state with said actual state or when checking whether a deviation of said actual state and said target state leaves a tolerance range.

14. The monitoring device of claim 1, wherein said monitoring device is configured to perform a comparison of said target state with said actual status in response to receiving an external data.

15. The monitoring device of claim 1, wherein said monitoring device includes a plurality of sensors of different types, wherein the evaluation unit is adapted to read out the sensors with different sampling rates depending on the type.

16. The monitoring device of claim 1, comprising an interface configured for data transfer from or to a database including a portal or an internet-based user-accessible database, wherein the data transferable via said interface comprises at least one of the following data:
- the current location of the animal;
- address data of the animal owner; and,
- data on animal species or animal breed.

17. The monitoring device of claim 1, comprising a device for generating electrical energy from movements of the animal, which device can be operated by a control unit as an actuator for emitting a vibration signal to the animal by supplying electrical energy.

18. The monitoring device of claim 1, wherein said at least one sensor for sensing the vital function of the animal wearing the carrier comprises a sensor for electromagnetic waves for detecting a vital function of an animal on the basis of received electromagnetic waves including light including infrared and ultraviolet light, said sensor comprising a radiation source for a sensing signal in the form of electromagnetic waves with adjustable spectral range for sensing a vital function by the sensor.

19. The monitoring device of claim 1, comprising at least one sensor in a form of an autonomous sensor node configured to be attachable to an animal for sensing a vital function, the sensor node comprising:
- at least one signal pickup;
- at least one autonomous or central power supply;
- at least one analog or digital interface; and
- at least one analog or digital timer;
- wherein the sensor node is further configured to be at least temporarily connected to a wired or wireless or optical network with an evaluation unit attachable to the animal separately from the sensor node or with at least one further autonomous sensor node that is attachable to the animal separately from the sensor node.

20. The monitoring device of claim 19, comprising at least one autonomous sensor node having any of the features:
- at least one unit for sensing and a display configured to display a sensor status;
- at least one analog or digital signal processing unit; and,
- at least one analog or digital volatile or digital non-volatile signal memory.

21. An arrangement comprising a monitoring device as claimed in claim 1, wherein the monitoring device comprises a wireless transmitter configured to transmit an output signal, wherein the arrangement comprises a wireless receiver configured to communicate with a control unit, and wherein said control unit is configured to drive at least one actuator in response to a reception of the output signal.

22. A monitoring device for monitoring vital functions, the monitoring device comprising:
- at least one carrier configured to be attachable to an animal and comprising at least one sensor configured to sense a vital function of the animal wearing said carrier, and an evaluation unit configured to communicate with said at least one sensor; and
- an output configured to output an output signal;
- wherein said evaluation unit further comprises a signal generator and a data storage unit;
- wherein said signal generator being configured to emit signals at time intervals; and,
- wherein said evaluation unit is configured to store at least one sensed value of a vital function sensed by said sensor in response to a signal from said signal generator and to store said at least one sensed value in said data storage unit and to add at least one of a data corresponding to said at least one sensed value to said data storage unit;
- wherein said evaluation unit is further configured to access stored sensor data in said data storage unit and to autonomously define a target state based on said accessed stored data, and to determine the values of vital functions for said target state for the animal and independent of comparative data of other animals;

said evaluation unit being further configured to determine an actual state on the basis of said data sensed after a definition of said target state and stored in said data storage unit;

said evaluation unit being configured to compare said actual state with said target state and in case of a deviation of said actual state from said target state or in case of a correspondence between said actual state and said target state, to output an output signal via the output; wherein:

said target state has target parameters associated therewith, the target parameters include at least one of a pulse rate; a body temperature; a blood oxygen; a respiration rate;

said target parameters including at least one of a frequency distribution of the pulse rate and a rate of decrease of the pulse rate as sensed by a pulse rate sensor following a movement phase of the animal sensed by an acceleration sensor;

said evaluation unit is configured to statistically evaluate data of at least one vital function stored in said data storage unit and determine said target state on the basis of at least one statistical parameter obtained from the evaluation, wherein the statistical parameter includes at least one of an average, a variance, a full width at half maximum of a frequency distribution, or a correlation coefficient; and wherein said evaluation unit is configured to continuously update said target state using data sensed by said sensor and stored in said data storage unit.

* * * * *